United States Patent
Wilshe

(10) Patent No.: US 11,000,541 B1
(45) Date of Patent: May 11, 2021

(54) MEDICINE COMPOSITION FOR FACILITATING TREATING ORGANS OF A MAMMAL

(71) Applicant: Donald Richard Wilshe, Parrish, FL (US)

(72) Inventor: Donald Richard Wilshe, Parrish, FL (US)

( * ) Notice: Subject to any disclaimer, the term of this patent is extended or adjusted under 35 U.S.C. 154(b) by 0 days.

(21) Appl. No.: 17/173,995

(22) Filed: Feb. 11, 2021

Related U.S. Application Data

(60) Provisional application No. 63/022,970, filed on May 11, 2020, provisional application No. 63/029,263, filed on May 22, 2020, provisional application No. 63/046,013, filed on Jun. 30, 2020, provisional application No. 63/045,993, filed on Jun. 30, 2020.

(51) Int. Cl.
| | |
|---|---|
| *A61K 33/00* | (2006.01) |
| *A61K 9/107* | (2006.01) |
| *A61K 9/06* | (2006.01) |
| *A61K 9/00* | (2006.01) |
| *A61K 47/46* | (2006.01) |
| *A61P 31/04* | (2006.01) |
| *A61K 47/44* | (2017.01) |

(52) U.S. Cl.
CPC ............ *A61K 33/00* (2013.01); *A61K 9/0014* (2013.01); *A61K 9/06* (2013.01); *A61K 9/107* (2013.01); *A61K 47/44* (2013.01); *A61K 47/46* (2013.01); *A61P 31/04* (2018.01)

(58) Field of Classification Search
None
See application file for complete search history.

(56) References Cited

U.S. PATENT DOCUMENTS

2011/0190393 A1* 8/2011 Gore ................. A61P 25/08
514/547

* cited by examiner

*Primary Examiner* — Nannette Holloman

(57) ABSTRACT

Disclosed herein is a medicine composition for facilitating treating organs of a mammal, in accordance with some embodiments. Accordingly, the medicine composition may include carbanions and a diluting agent. Further, a carbanion of the carbanions may include a carbon atom. Further, the carbon atom may include a formal charge of −1. Further, the diluting agent may be capable of combining with the carbanions for forming at least one appliable form of the medicine composition. Further, a ratio of the diluting agent to the carbanions by volume ranges from 512:1 to 32:1. Further, the combining facilitates applying of the at least one appliable form of the medicine composition to at least one organ of the mammal.

20 Claims, 31 Drawing Sheets

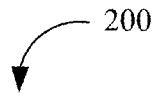

```
                                    ┌─ 200
                                    ↓
```

TRANSFORMING, USING AT LEAST ONE APPLICATION DEVICE, THE MEDICINE COMPOSITION INTO AT LEAST ONE APPLIABLE FORM, WHEREIN THE MEDICINE COMPOSITION COMPRISES CARBANIONS AND A DILUTING AGENT, WHEREIN A CARBANION OF THE CARBANIONS COMPRISES A CARBON ATOM, WHEREIN THE CARBON ATOM COMPRISES A FORMAL CHARGE OF -1, WHEREIN THE DILUTING AGENT IS CAPABLE OF COMBINING WITH THE CARBANIONS FOR FORMING THE AT LEAST ONE APPLIABLE FORM OF THE MEDICINE COMPOSITION, WHEREIN A RATIO OF THE DILUTING AGENT TO THE CARBANIONS BY VOLUME RANGES FROM 512:1 TO 32:1   202

APPLYING, USING THE AT LEAST ONE APPLICATION DEVICE, AT LEAST ONE DOSAGE OF THE AT LEAST ONE APPLIABLE FORM OF THE MEDICINE COMPOSITION ON AT LEAST ONE ORGAN OF THE MAMMAL BASED ON THE TRANSFORMING, WHEREIN THE APPLYING OF THE AT LEAST ONE DOSAGE OF THE AT LEAST ONE APPLIABLE FORM OF THE MEDICINE COMPOSITION FACILITATES THE TREATING OF THE AT LEAST ONE ORGAN OF THE MAMMAL   204

| Species | Fluconazole | Posaconazole | Voriconazole | Itraconazole | Echinocandin | Amphotericin Formulations | Flucytosine |
|---|---|---|---|---|---|---|---|
| Candida albicans | +++ | +++ | +++ | +++ | +++ | +++ | + |
| Candida glabrata | ± | ++ | ++ | + | +++ | ++ | + |
| Candida krusei | − | ++ | ++ | ± | +++ | ++ | + |
| Aspergillus | − | ++ | +++ | ++ | +++ | ++ | − |
| Blastomyces | + | ++ | ++ | +++ | − | +++ | − |
| Coccidioides | ++ | + | ++ | + | − | +++ | − |
| Histoplasma capsulatum | ± | ++ | ++ | +++ | − | +++ | − |
| Sporotrix schenckii | − | + | + | +++ | − | +++ | − |
| Cryptococcus neoformans | ++ | ++ | ++ | + | − | +++ | + |
| Mucor | − | ++ | − | ± | − | +++ | − |

+++: 1st line therapy, most clinical activity; ++: 2nd line therapy, less clinical activity; +: 3rd line therapy, even less clinical activity; ±: possible clinical activity; −: no clinical activity
c Generally used in combination therapy with amphotericin formulations
Source: References 1, 2, 4-6, 8, 9, 12, 14

FIG. 21

| Drug | Dosage Range | Fungal Lung Infection |
|---|---|---|
| Itraconazole | 200 mg po twice daily | Histoplasmosis, blastomycosis, sporotrichosis |
|  | 400 mg po daily | Coccidioidomycosis, cryptococcosis |
|  | 400-600 mg po daily | Aspergillosis |
| Fluconazole | 400 mg po daily | Coccidioidomycosis, cryptococcosis, candidiasis |
| Voriconazole | 6 mg/kg q12h × 1 day, then 4 mg/kg q12h IV | Aspergillosis |
|  | Salvage therapy dose: 200 mg po q12h |  |
| Posaconazole | 200 mg po 4 times daily, then (after disease stabilization) 400 mg po twice daily | Aspergillosis |
|  | 800 mg po daily in 2-4 divided doses | Mucormycosis |
| Caspofungin | 70 mg IV × 1, then 50 mg IV daily | Aspergillosis, candidiasis |
| Micafungin | 100-150 mg IV daily | Aspergillosis |
|  | 100 mg IV daily | Candidiasis |
| Anidulafungin | 200 mg IV × 1, then 100 mg IV daily | Candidiasis |
| Conventional AmB | 0.7 mg/kg/day | Histoplasmosis |
|  | 0.7-1 mg/kg/day | Coccidioidomycosis, sporotrichosis, cryptococcosis, mucormycosis |
|  | 0.5-0.7 mg/kg/day | Blastomycosis, coccidioidomycosis, mucormycosis, Aspergillosis, candidiasis, cryptococcosis |
| Liposomal AmB | 5 mg/kg/day |  |
|  | 3-5 mg/kg/day |  |
| Flucytosine | 100 mg/kg/day IV | Cryptococcosis, candidiasis |

*For adults with normal renal and hepatic function. ‡Currently used in combination therapy with AmB formulations...

Source: References 1, 2, 4-6, 8, 9, 12, 14

| | | Analysis (as rec'd) | Analysis (dry weight) | Total content, fertigation (as rec'd) |
|---|---|---|---|---|
| NUTRIENTS | | | | |
| *Nitrogen* | | | | |
| Total Nitrogen | % | 5.42 | 9.35 | 0.508 |
| Organic Nitrogen | % | 5.26 | 9.07 | 0.493 |
| Ammonium Nitrogen | % | 0.165 | 0.285 | 0.015 |
| Nitrate Nitrogen | % | < 0.01 | --- | --- |
| *Major and Secondary Nutrients* | | | | |
| Phosphorus | % | < 0.05 | --- | --- |
| Phosphorus as P2O5 | % | < 0.1 | --- | --- |
| Potassium | % | < 0.05 | --- | --- |
| Potassium as K2O | % | < 0.1 | --- | --- |
| Sulfur | % | < 0.05 | --- | --- |
| Calcium | % | 0.02 | 0.03 | 0.002 |
| Magnesium | % | < 0.01 | --- | --- |
| Sodium | % | 0.04 | 0.069 | 0.004 |
| *Micronutrients* | | | | |
| Zinc | ppm | < 20 | --- | --- |
| Iron | ppm | < 50 | --- | --- |
| Manganese | ppm | < 20 | --- | --- |
| Copper | ppm | < 20 | --- | --- |
| Boron | ppm | < 20 | --- | --- |
| OTHER PROPERTIES | | | | |
| Moisture | % | 42.03 | | |
| Total Solids | % | 57.97 | | |
| C:N Ratio | | 8.2:1 | --- | |
| Total Carbon | % | 44.3 | 76.47 | |
| Chloride | % | < 0.01 | --- | |
| pH | | 10.40 | | |
| Density | lbs./gal | 9.39 | | |

FIG. 29

MEDICINE COMPOSITION FOR FACILITATING TREATING ORGANS OF A MAMMAL

FIELD OF THE INVENTION

Generally, the present disclosure relates to the field of Drug, bio-affecting, and body treating compositions. More specifically, the present disclosure relates to a medicine composition for facilitating treating organs of a mammal.

BACKGROUND OF THE INVENTION

When it comes to treatment for diseases caused by organisms such as viruses bacteria, fungi, insects, it may be a financial issue for people who are in need of treatment. Further, the organism such as the viruses, the bacterial, fungi, insects, etc. may infect organs of mammal such as humans causing the diseases. Further, treatments for infectious viruses causing the diseases may vary in price. For the very common and well-known virus, the materials needed to produce a treatment for the said virus will most likely be relatively cheap. On the other hand, for the more rare and undiscovered virus, the materials needed to produce a treatment for the said virus will definitely be expensive as there are lesser known cases of the rare virus, and maybe more difficult to find a treatment. Another issue with infectious viruses is that not all of the viruses have been studied as there is an unknown number of undiscovered viruses. One prime example of an unknown virus was COVID-19. In December 2019, COVID-19 was newly discovered as an outbreak occurred from Wuhan, China. COVID-19 lead to an international pandemic. Due to the unknown virus COVID-19, the treatment for COVID-19 has yet been discovered even a few months after the discovery of the virus itself. The complexity of finding and producing a treatment for COVID-19 is extremely difficult due to the anomaly of the newly discovered virus.

Existing compositions for facilitating treating organs of a mammal are deficient with regard to several aspects. For instance, existing compositions do not perform treatment of various organs of a mammal. Furthermore, existing compositions do not eliminate viruses, bacteria, fungi, and insects present on various organs for treating the various organs. Moreover, existing compositions do not totally derive from organic matter.

Therefore, there is a need for an improved medicine composition for facilitating treating organs of a mammal that may overcome one or more of the above-mentioned problems and/or limitations.

SUMMARY OF THE INVENTION

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

Disclosed herein is a medicine composition for facilitating treating organs of a mammal, in accordance with some embodiments. Accordingly, the medicine composition may include carbanions and a diluting agent. Further, a carbanion of the carbanions may include a carbon atom. Further, the carbon atom may include a formal charge of −1. Further, the diluting agent may be capable of combining with the carbanions for forming at least one appliable form of the medicine composition. Further, a ratio of the diluting agent to the carbanions by volume ranges from 512:1 to 32:1. Further, the combining facilitates applying of the at least one appliable form of the medicine composition to at least one organ of the mammal.

Further disclosed herein is a method for facilitating treating organs of a mammal using a medicine composition, in accordance with some embodiments. Accordingly, the method may include a step of transforming, using at least one application device, the medicine composition into at least one appliable form. Further, the medicine composition may include carbanions and a diluting agent. Further, a carbanion of the carbanions may include a carbon atom. Further, the carbon atom may include a formal charge of −1. Further, the diluting agent may be capable of combining with the carbanions for forming the at least one appliable form of the medicine composition. Further, a ratio of the diluting agent to the carbanions by volume ranges from 512:1 to 32:1. Further, the method may include a step of applying, using the at least one application device, at least one dosage of the at least one appliable form of the medicine composition on at least one organ of the mammal based on the transforming. Further, the applying of the at least one dosage of the at least one appliable form of the medicine composition facilitates the treating of the at least one organ of the mammal.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

FIG. 2 is a flowchart of a method for facilitating treating organs of a mammal using a medicine composition, in accordance with some embodiments.

FIG. 17 is a table of an initial screen of pathogens vs. dilution of Formula S-101, in accordance with some embodiments.

FIG. 19 is a table of the second screen of pathogens vs. dilution of Formula S-101, in accordance with some embodiments.

FIG. 20 is a table of a subset of the second screen of pathogens vs. dilutions of Formula S-101, in accordance with some embodiments.

FIG. 21 is a table of therapeutic options for fungal lung infections.

FIG. 22 is a table of antifungal treatment options.

FIG. 29 is a table of compositional elements of the medicine composition, in accordance with some embodiments.

DETAIL DESCRIPTIONS OF THE INVENTION

Figure 1:
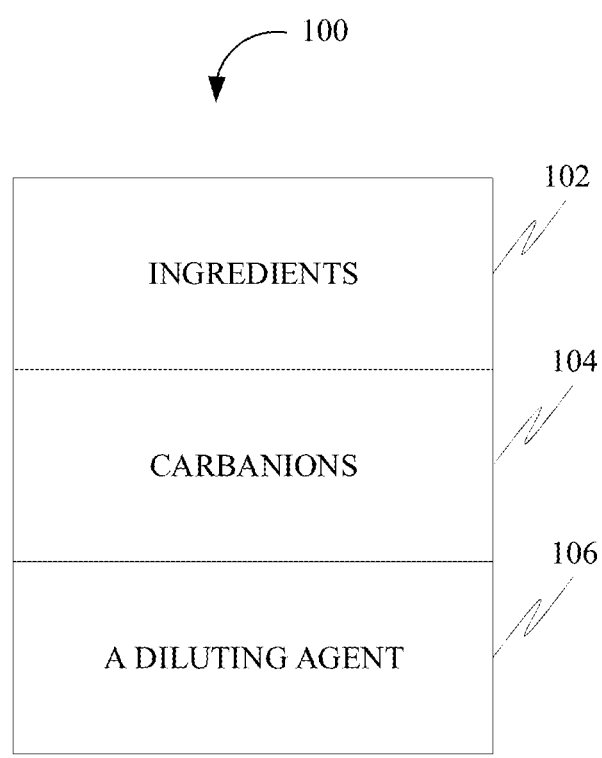
FIG. 1 is a table listing ingredients of a medicine composition for facilitating treating organs of a mammal, in accordance with some embodiments.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim limitation found herein and/or issuing here from that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible.

For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the claims found herein and/or issuing here from. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of a medicine composition for facilitating treating organs of a mammal, embodiments of the present disclosure are not limited to use only in this context.

Overview:

The present disclosure describes a medicine composition for facilitating treating organs of a mammal. Further, the medicine composition may include carbanions. Further, the carbanions facilitate the treating of the organs of the mammal.

Further, the present disclosure describes a method for treating the organs using the medicine composition.

Further, the present disclosure may provide a treatment of the contagious and infectious lung bacterial and fungi diseases. Furthermore, the present disclosure may provide a cheap and cost-efficient treatment for the contagious and/or infectious lung bacterial, and fungi diseases. The present disclosure also provides a treatment to cure multiple known lung bacterial and fungi diseases and potentially undiscovered lung bacterial and fungi diseases. The present disclosure may include a mining stage, a mixture stage, a production stage, and a treatment stage.

Further, the present describes carbanions for facilitating COVID-19 Treatment, Control of Viruses, Fungi, Bacteria, and Insect, and Adjuvant & Nebulized Drug Delivery to Lungs and Skin of the Mammal.

Further, the carbanions may include individual atoms. Further, the carbanions may include negatively charged carbon atoms. Further, the negatively charged carbon atom may include a formal charge of −1. Further, the negatively charged carbon atoms may be created by making use of the physical chemistry of carbon atoms. Further, the physical chemistry may be the study of macroscopic, atomic, subatomic, and particulate phenomena in chemical systems in terms of the principles, practices, and concepts of physics such as motion, energy, force, time, thermodynamics, quantum chemistry, statistical mechanics, analytical dynamics and chemical equilibrium. Further, the carbanions may be created by making the use of the physical chemistry of the carbanions. Further, the physical chemistry may be the study of macroscopic, atomic, subatomic, and particulate phenomena in chemical systems in terms of the principles, practices, and concepts of physics such as motion, energy, force, time, thermodynamics, quantum chemistry, statistical mechanics, analytical dynamics and chemical equilibrium. Further, the physical chemistry is the study of how matter behaves on a molecular and atomic level and how chemical reactions occur. Based on the analyses, physical chemists may develop new theories, such as how complex structures are formed. Physical chemists often work closely with materials scientists to research and develop potential uses for new materials. Further, the physical chemistry may be used in observing the assembly of molecules and determining, measuring, and quantifying the assembly of the molecules. Further, the physical chemistry may allow for assembling of molecules in crystals and solutions and observing and measuring of the arrangements of atoms and molecules and aggregates of the atoms and the molecules in the solutions as well as in crystals and various properties the aggregates of surfactants impart to a product. Further, diffraction, infrared, and microscopy methods are used for observing the assembly of the molecules and further determining, measuring, and quantifying the assembly of the molecules. Further, the physical chemistry may be used for developing better ways to measure and quantify aspects of the ingredients for developing better products. Further, physical chemistry provides an understanding of the physical properties of atoms and molecules, the way chemical reactions work, and what these properties reveal. Further, the physical chemistry involves analyzing materials, developing methods to test and characterize the properties of materials, developing theories about these properties, and discovering the potential use of the materials. Using sophisticated instrumentation and equipment has always been an important aspect of physical chemistry. Most physical chemistry labs are full of analytical instruments, which may include lasers, mass spectrometers, nuclear magnetic resonance, and electron microscopes. Further, the physical chemistry may provide an understanding of chemical properties and describes the behavior of chemicals using theories of physics and mathematical computations. Further, the properties and reactions of the chemicals may be predicted using the physical chemistry. Physical chemistry describes fundamental physical characteristics of material be it solid, liquid, or gas. Further, the physical chemistry may be used for the development of materials, including plastics, ceramics, catalysis, electronics, fuel, batteries, surfactants, and colloids, and personal care products.

Further, the carbanions may include carbon atoms. Further, the carbon atoms may be associated with CO2 (carbon dioxide) gas. Further, an average person breathes out around 500 liters of the greenhouse gas CO2, which amounts to around 1 kg or 2.3 pounds of mass. Further, the world's population is around 6.8 billion, collectively breathing out around 2500 million tons of the CO2, which is around 7 percent of the annual CO2 tonnage churned out by the burning of fossil fuel around the world. Further, the CO2 breath out by the average person may be a part of a natural cycle, by which the body of the average person may convert carbohydrates from CO2-absorbing plants into energy, plus water and CO2. Further, the average person may breathe the carbon atoms of the CO2 and consume the carbon atoms of plants.

Further, the carbanions may be created using pico-technology. Further, the pico-technology is one of the most promising realms of science, bringing new products to society in many industries. Further, the pico-technology is only about particle having size 1000 times smaller than a nanometer. The product is made mostly of Carbon and Nitrogen and trace elements. There are 25,400,000 nanometers in one inch. There are 1000 Pico meters in a nanometer; Therefore an inch has 25,400,000,000 Pico meters, and a human hair is 80,000,000 to 100,000,000 Pico meters thick. Further, pico-technology may be described as involving the alteration of the structure and the chemical properties of individual atoms through the manipulation of energy states of electrons within the individual atoms to produce states with unusual properties, producing some form of exotic atoms. Further, the pico-technology may allow the usage of atoms singularly. Further, the pico-technology may be used for the fabrication of structures where atoms may be positioned with sub-nanometer accuracy. This may be important where interaction with a single atom or molecule may be desired. Further, the pico-technology may be used for altering electron distributions around atoms to promote surface energy to achieve inhibited infection without potential nanomaterial toxicity concerns. Further, the pico-technology may be used to describe the control of electron distribution around the atoms to provide desirable properties. Further, the control of the electron distribution may greatly change surface energy and, thus, the way that proteins adsorb onto a material. Further, the excitement or rearrangement of electrons around the atoms may influence many cellular functions including cell movement, intracellular transport to organelles, adhesion, growth, and ECM formation. Further, the pico-technology may control cellular microtubules (MTs). MTs are cylindrical cellular formations 25 nm in diameter, and they are made out of tubulins. Dynamic instability due to MT plus end-binding proteins also called "plus end-tracking proteins", are able to "surf" the dynamic ends of the MTs. Further, when tips are expressed as green fluorescent proteins, the fluorescence is the brightest at the MT and decreases in intensity toward the minus end of the MT, forming a comet tail. Further, external stimulation is used to excite the MT and end-binding proteins to promote the movement of cells using the pico-technology. This may be a less toxic manner through which to alter surface energy to increase tissue growth since electron distributions may be changed for numerous macro-, micro-, or nanomaterials. Further, the pico-technology may be used to reduce the toxicity in any macro-, micro-, or nanomaterials by exciting electrons. The change in electron distribution, along with the associated charge redistribution, may alter surface energetics to change the adsorption of certain proteins (as well as cellular functions).

Further, the carbanions may be created using Femto-technology. Further, the Femto-technology may be used for creating 8-octet, 9-nonet, 10-dectet, 11-undectet, and 12-duodectet by addition of electron on a carbon atom. Further, the Femto-technology may be used for matter manipulation for modifying the carbon atom.

Further, the carbanions may be individual atoms or atoms in covalent bonds. Further, the individual atoms alone or the atoms in the covalent bonds may create powerful electromechanical reactions to disassemble organic material, one atom per atom at a time. Further, the individual atoms alone or the atoms in the covalent bond may work on the fungi, the bacteria, or the viruses to eliminate the fungi, the bacteria, or the viruses. Further, the individual atoms alone or the atoms in the covalent bond may eliminate Shingles, Basil Cell Cancer, Squamous Cell Cancer, Poison Ivy, Oak, Sumac, Diabetic Ulcers, Wounds, Plaque Psoriasis, Genetic Blistering, Head lice, and Whopping Cough of humans. Further, the individual atoms alone or the atoms in the covalent bond may regenerate or grow the skins on the humans.

Further, a Pico Skin may include the carbanions. Further, the Pico Skin in a 1/512 solution may be used for treating and curing abrasions on skins.

Further, the carbanions may include PicoMed Skin Virus's, PicoMed Skin Acne Cleans, PicoMed Skin Actinic Keratosis, PicoMed Skin Alopecia Areata, PicoMed Skin Athlete's Foot, PicoMed Skin Atopic Dermatitis, PicoMed Skin Atopic Eczema, PicoMed Skin Bacteria's, PicoMed Skin Barrier function, firmness and elasticity, PicoMed Skin Beauty Habits, Skin Care, and Makeup, PicoMed Skin Bed Bugs, PicoMed Skin Biofilms Cleanse, PicoMed Skin Biofilms Flush Cleanse, PicoMed Skin Birthmarks and Other Skin Pigmentation Problems, PicoMed Skin Black Seed-like "specks" or "Dots" from Lesions Cleanse, PicoMed Skin Black Tar-like substance from skin pores Cleanse, PicoMed Skin Blastomycosis, PicoMed Skin Boils, PicoMed Skin Bruises, PicoMed Skin Bug Bites and Stings, PicoMed Skin Burns, PicoMed Skin Cancer, PicoMed Skin Canker Sores Health, PicoMed Skin Cellulitis, PicoMed Skin Chiggers (Bites), PicoMed Skin Collembola, PicoMed Skin Conditions, PicoMed Skin Contact Dermatitis, PicoMed Skin Corns, PicoMed Skin Crust/Scab/Callus like Formations Cleanse, PicoMed Skin Cuts, Scrapes and Puncture Wounds, PicoMed Skin Cysts, PicoMed Skin Dark or black specks in your sheets Cleanse, PicoMed Skin Dark or black specks on your body Cleanse, PicoMed Skin Dercum's Syndrome, PicoMed Skin Diabetics' Dry Skin Relief Rehydrating Lotion, PicoMed Skin Diaper Rash, PicoMed Skin Discolored Cleanse Cleanse, PicoMed Skin Divots in my skin are now flush Cleanse, PicoMed Skin Dry Skin, PicoMed Skin Eczema Relief Cream, PicoMed Skin Erythema Nodosum, PicoMed Skin Extremely Dry, Rough, Callus, PicoMed Skin Fibers Black Cleanse, PicoMed Skin Fibers Blue Cleanse, PicoMed Skin Fibers Red Cleanse, PicoMed Skin Filaments Cleanse, PicoMed Skin Fire Ant Bites Infection Prevention, PicoMed Skin Folliculitis, PicoMed Skin Freckles, PicoMed Skin Frostbite, PicoMed Skin Fungal Nails, PicoMed Skin Fungals and Molds Cleanse, PicoMed Skin Fungi's, PicoMed Skin Granulating Tissue hard and crystal like Cleanse, PicoMed Skin Granules Above/Below Skin Cleanse, PicoMed Skin Hair Loss, PicoMed Skin Hand Cream moisturizes, PicoMed Skin Healing Cleanse, PicoMed Skin Heat Rash, PicoMed Skin Hematoma, PicoMed Skin Herpes Simplex Infections (Non-Genital), PicoMed Skin Hives, PicoMed Skin Hyperhidrosis, PicoMed Skin Genetic Blistering Disease, PicoMed Skin Inflammation yes or no Cleanse, PicoMed Skin Ingrown Hair, PicoMed Skin Ingrown Toenail, PicoMed Skin Intertrigo, PicoMed Skin Keratin 2006 For Nails, Skin and Hair, PicoMed Skin Itch, PicoMed Skin Jock Itch, PicoMed Skin Keloid, PicoMed Skin Keratosis Pilaris, PicoMed Skin Lesions Cleanse, PicoMed Skin Lesions—Itchy, Sore, Painful, Slow Healing Cleanse, PicoMed Skin Lesions with Fuzzballs Cleanse, PicoMed Skin Lichen Planus, PicoMed Skin Lichen Sclerosus, PicoMed Skin Loss Its Elasticity And Sags, PicoMed Skin Melasma, PicoMed Skin Moisturizing Cream For Diabetis Skin, PicoMed Skin Moles, PicoMed Skin Molluscum Contagiosum, PicoMed Skin New Wiry or Thick Hair Over Lesions Before Cleanse, PicoMed Skin Oozing Cleansev, PicoMed Skin Open Sores, Wounds or Cuts Cleanse, PicoMed Skin Parasites Cleanse, PicoMed Skin Pigment Changes Cleanse, PicoMed Skin Pilonidal Cyst, PicoMed Skin Pimples long lasting Cleanse, PicoMed Skin Pityriasis Rosea, PicoMed Skin Poison Ivy, PicoMed Skin Poison Oak, PicoMed Skin Postherpetic Neuralgia, PicoMed Skin Psoriasis, PicoMed Skin Psoriatic Arthritis, PicoMed Skin Rash, PicoMed Skin Rashes Cleanse, PicoMed Skin Red Cleanse, PicoMed Skin Rhinoplasty, PicoMed Skin Ringworm, PicoMed Skin Rosacea, PicoMed Skin Rothmund-Thomson Syndrome, PicoMed Skin Scabbing Cleanse, PicoMed Skin Scabies, PicoMed Skin Scars, PicoMed Skin Seborrhea, PicoMed Skin Seborrheic Dermatitis, PicoMed Skin Seed Like specks Cleanse, PicoMed Skin Sensation Biting Cleanse, PicoMed Skin Sensation Burning Cleanse, PicoMed Skin Sensation Crawling Cleanse, PicoMed Skin Sensation Creeping Cleanse, PicoMed Skin Sensation Itching Cleanse, PicoMed Skin Sensation Pain Cleanse, PicoMed Skin Sensation Pinching Cleanse, PicoMed Skin Sensation Pricking Cleanse, PicoMed Skin Sensation Stinging Cleanse, PicoMed Skin Sensation Worms or wire like structures Cleanse, PicoMed Skin Sensitivity Cleanse, PicoMed Skin Shards hard and crystal like glass Cleanse, PicoMed Skin Shingles (Herpes Zoster), PicoMed Skin Shingles and Pregnancy, PicoMed Skin Spider Bites (Black Widow and Brown Recluse), PicoMed Skin Spreading Cleanse, PicoMed Skin Stretch Marks, PicoMed Skin Strongyloides, PicoMed Skin Summer Skin Hazards, PicoMed Skin Sun Protection and Sunscreens, PicoMed Skin Sun Safety, PicoMed Skin Sunburn and Sun Poisoning, PicoMed Skin Sun-Sensitive Drugs (Photosensitivity to Drugs), PicoMed Skin Texture—Leathery, callus-like developed Cleanse, PicoMed Skin Tinea Versicolor, PicoMed Skin Tissue granulating and filling Cleanse, PicoMed Skin Venous Stasis Ulcer, Varicose Ulcers, or Ulcus Cruris, PicoMed Skin Vitiligo, PicoMed Skin Warts (Common Warts), PicoMed Skin Weber-Christian Disease, PicoMed Skin Wrinkles, etc.

Further, the present disclosure describes pico-products comprising the carbanions. Further, the pico-products may include a PicoMed, a PicoCare, PicoSkin, etc. Further, the pico-products comprising the carbanions may have the following characteristics:

1). No harm to air (no GWC, ODC, VOHAP, or VOC) soil, or water.
2). cannot be made of organic chemistry, graphene, or nanotechnology, just single atom Pico technology or physical chemistry
3). The goals are primary distribution as an OTC product.
4). It must be made of atomic elements and not molecules.
5). Must be able to kill all pests, be it bacteria, fungi, viruses, and insects.
6). Must be able to deep clean and grow skin and heal wounds just days not weeks
7). Must be able to penetrate the shields of all pests.
8). Must be approved at the State and or Federal FDA or better be exempt.
9). Must be safe for humans, bees, birds, and animals—zero side effects.
10). Must be made of 100% new organic carbon.
11). No Chemicals
12). No Biologicals
13). No Nanotechnology
14). No Graphene
15). No Molecules
16). Eliminate Sickness Further, the pico-products may be formed using the physical chemistry. Further, the pico-products may 89% Biobased Content.

Further, the pico-products may be used for the elimination of vital elements in bacteria, insects, fungi, and viruses.

Further, the pico-products is configured for eliminating the cell membrane of the bacteria and puncturing the cell membrane. Further, the eliminating and the puncturing of the cell membrane may drain proteins and lipids from the bacteria.

Further, the pico-products is configured for eliminating the cellulose and chitin of the fungus.

Further, the pico-products is configured for eliminating strands of a nucleic acid of the virus, either DNA or RNA of the virus, and protective protein coat of the virus (the capsid), or a lipid envelope of the virus, surrounding the protein of the virus.

Further, the pico-products is configured for dissolving cellular membranes of the insects, eliminating cells desiccation of the insects, eliminating or penetrating cellular metabolism of the insects, dissolving cuticles of the insects, eliminating lubrication joints of the insects leading to paralysis, stripping the protective shields of the insects, eliminating exoskeleton structure of the insects, and dissolving chitin and protein substances of the insects.

Further, the pico-products immediately impacts the exoskeleton structure of the pest upon contact by disrupting the molecular structure of the chitin and other protein substances that protect the insect. This mechanism of action triggers the rapid and irreversible deterioration of the insect's spiracles and tracheal system, resulting in suffocation. Further, the pico-products kills insects with the elimination of chitin. Further, the chitin is a polysaccharide and a carbohydrate that has a chain of sugar molecules. Further, chitin has a structure like cellulose. Additionally, the chitin may be present in the exoskeletons of the insects.

Further, the pico-products benefit from the revolutionary method of insect control with an absence of undesirable side effects on human health and no harm to the ecosystem. Additionally, unlike standard insecticides in use today, no built-in resistance may be developed by the targeted insects.

Further, the pico-products may be mechanical in primary sequential steps. Further, a first step is a direct interaction between the surface and the outer membrane of the pests, causing the membrane to rupture and leak fluids, proteins, and nutrients.

Further, the pico-products may attack pests at the atom level. Further, at the atom level, the shield of the pests starts to disassemble. Further, the pico-products kills the pests by eliminating the shield.

Lastly, in a few more ways, the pico-products' electromechanical effect may affect the pests:

There may be a second step related to the holes in the outer membrane, through which the pests lose vital nutrients, protein, water, and components, causing a general weakening of the pests.

Electromechanical effect of the pico-products may affect pests, the pico-products penetrates and dissolves lipid of cellular membranes of the pests.

This causes cell desiccation to leak water, proteins, and nutrients and collapse.

By interfering with cellular metabolism during metamorphosis.

By dissolving cuticles, the lubrication in the insect and joints of the insects, leading to paralysis.

By stripping the pests' protective shields (wax, biofilm, etc.), rendering the pests defenseless against subsequent treatment.

The extracts impact the exoskeleton structure of the pests upon contact by disrupting the molecular structure of the chitin and other protein substances that protect the insect.

The extracts may have the ability to penetrate complex hydrocarbon chains and disintegrate the insects.

The change in the environment for growth with PH from acidophils and neutrophils to alkaliphiles.

Further, the pico-products may be configured for punching holes in a cell of the pests. Further, the punching of the holes in the cell breaches a main defense of the cell. Further, an unopposed stream of the pico-products enters the cell. This puts several vital processes inside the cell in danger. Further, the pico-products overwhelm the inside of the cell and obstruct cell metabolism (i.e., the biochemical reactions needed for life). Further, the pico-products bind to enzymes of the cell halting the activity of the cell. Further, the pests no longer "breathe", "eat", "digest", "reproduce" or "exist".

Further, an outer membrane of the cell, including that of a single cell organism like pests, is characterized by a stable electrical micro-current. This is often called "transmembrane potential", and is literally, a voltage difference between the inside and the outside of a cell. It is strongly suspected that when a pest comes in contact with the pico-products, short-circuiting of the current in the cell membrane may occur. Further, the current weakens the outer membrane and creates holes for leaking water, proteins, and nutrients from the cell.

Further, the pico-products effects fast and affect such a wide range of pests. The experiences observed explain the speed with which pests and other pests perish on pico-products surfaces by the multi-targeted effects. Further, membrane perforation may inhibit any given enzyme that "stands in its way," and stops the cell from transporting or digesting nutrients, repairing its damaged membrane, and breathing or multiplying. This makes the pest harmless to humans, birds, and animals. This has no side effects or harm on human, birds, and animal health. These solutions do not harm mammal cells nor do the solutions attack the neurological systems of humans, birds, and animals. Further, the pico-products may lyse cells to extract protein or organelles, or to permeabilize the membranes of living cells.

The pico-products dissolves lipids from cell membranes making the cell membranes permeable to antibodies. Because the organic solvents also coagulate proteins, the pico-products may be used to fix and permeabilize cells at the same time. Saponin interacts with membrane cholesterol, selectively removing it and leaving holes in the membrane. Permeabilization is the process of making something, such as a membrane or cell wall, permeable. Lyse is a verb referring to the process of lysis, the death of a cell. Lysis refers to the breaking down of the membrane of a cell, often by viral, enzymic, or osmotic mechanisms that compromise cell integrity. A fluid containing the contents of lysed cells is called a lysate. In molecular biology, biochemistry, and cell biology laboratories, cell cultures may be subjected to lysis in the process of purifying the components, as protein purification, DNA extraction, RNA extraction, or purifying organelles.

Trophobiosis Cycle: Pesticides weaken plants. Weakened plants open the door to pests and disease. Further, the pesticides precipitate pest attacks and disease susceptibility, and thus the pesticides induce a cycle of further pesticide use.

Further, the pico-products may include a PicoMed. Further, the PicoMed may be made of only atoms 1000 times smaller than nanometer and made of Femto-technology (Electrons, Protons, Neutrons) elements.

Further, the present disclosure describes a composition comprising carbanions. Further, the carbanions are created using picotechnology. Further, the picotechnology works atom to atom for mechanical disassembly of Virus, Bacteria, Insect, and Fungi control. Further, a single drop of the composition may include 5 sextillion charged atoms. Further, the charged atoms restrict viruses' elemental mode of action by eliminating strands of nucleic acid, either DNA or RNA, and a protective protein coat (the capsid), or a lipid envelope, surrounding the protein of the viruses.

Further, the present disclosure describes a composition comprising carbanions for treating lung cancer. Further, a dosage of 3 drops of PicoMed given using a nebulizer for 5 consecutive days includes 75 sextillion carbanions for treating the lung cancer.

Further, the present disclosure describes a method and a process of creating carbanions that are used as a treatment for contagious and/or infectious viruses are shown. The method and process may include four stages. The process comprises a mining stage, a mixture stage, a production stage, and a treatment stage. The four different stages define the method and process of creating the carbanion to be used as a treatment for contagious and/or infectious viruses. The mining stage is the first stage of the method and process in the creation and usage of the carbanions. The mining stage is the initial stage in which the process of gathering and extracting carbon occurs. The gathering and extraction of carbon primarily occur from different parts of corn plants and tree oils. Some specific materials used in the process of mining are corn and tree oils. Corn has many parts to it such as leaves, stems, grain, roots, and cob. These different parts of corn contain many different elemental compositions such as carbon, oxygen, hydrogen, nitrogen, phosphorus, potassium, calcium, magnesium, sulfur, iron, silicon, aluminum, chlorine, and manganese. In summary, carbon is obtained through plants by the extraction of carbon dioxide. The mixture stage is the second stage of the method and process in the creation and usage of the carbanions. The mixture stage is the next stage after the mining stage. In the mixture stage, the blending and mixing of the ingredients along with the carbon from the mining stage occurs. The said ingredients are mixed in a proprietary sequence and time to create the solution that is ready to go under an exothermic reaction to create the carbanion. The production stage is the third stage of the method and process in the creation and usage of the carbanions. The production stage is the next stage after the mixture stage. In the production stage, an exothermic chemical reaction occurs to the said solution from the mixture stage. The solution that is created in the mixture stage is ready to undergo an exothermic reaction in order to produce the carbanion within the solution. An exothermic reaction is a chemical reaction that releases energy through light or heat, in this case, heat is applied and used. The exothermic reaction causes the carbon atoms within the solution to go from a neutral 6 neutrons, 6 protons, and 6 electrons configuration to a negatively charged 6 neutrons, 6 protons, and 8 electrons carbanion. The exothermic chemical reaction that is used is a process that robs electrons from other compounds and is given to the carbon atoms thus creating the carbanions. A carbanion has a highly negatively charged organic carbon, trivalent carbon atom that has eight electrons in its valence shell. The process of adding electrons is done by using temperature or pressure. The treatment stage is the fourth stage of the method and process in the creation and usage of the carbanions. During the treatment stage, the solution is ready to be used by the user with an infectious virus. The treatment for the user requires the user to be active with ingestion of the solution for over three days. The user is to apply the treatment three times a day, one in the morning, one in the afternoon, and one at night. Each treatment requires the user to insert three droplets of the solution into a nebulizer containing an ounce of water. The user is then to use the nebulizer to inhale the solution that is mixed with water within the nebulizer. The nebulizer will fog the carbanion into the lungs at 5 sextillion atoms of carbanion per drop, these carbanion atoms are to mechanically disassemble the vital parts of the virus as the atoms enter the virus. The interaction between atoms and ions occurs. When the highly charged carbanion is attached to a positive charge just like in nature, it removes the matter at an atom level. Since the user is applying the treatment three times per day for a duration of three days, approximately a total of 54 sextillion carbanion atoms are used in the process of treating the user with a virus. The carbanion binds to the body of the virus as well as puncture the membrane and drains vital fluids from the virus. The carbanions are made by using physical chemistry. Physical chemistry is simply the branch of chemistry concerned with interactions and transformation of materials. Unlike other branches, physical chemistry deals with the principles of physics underlying all chemical interactions, seeking to measure, correlate, and explain the quantitative aspects of reactions. Physical chemistry is the study of how matter behaves on a molecular and atomic level and how chemical reactions occur. Further, the physical chemistry involves the transformation of carbon into carbanions with an exothermic reaction. The carbanions have been approved by the USDA. Further, the carbanions form a product that is made from biomass and is also biobased. The product is nearly 90% carbon. The carbanions have been used in the treatment of multiple viruses in the past. Some viruses in which was treated by the use of the carbanions are arenavirus, banana mild mosaic virus, banana virus, bean pod virus, echovirus, hantavirus, influenza virus, morbillivirus, mosaic cucumber mosaic virus, parainfluenza virus, paramyxovirus, parvovirus B19, poxvirus vaccinia virus, rhinovirus, soybean mosaic virus, banana streak virus, togavirus, varicella-zoster virus, and *Yersinia pestis* virus.

The carbanions kill viruses by the elimination of strands of nucleic acid, either DNA or RNA, and a protective protein coat (the capsid), or a lipid envelope, surrounding the protein. The reason the carbanions can kill the said viruses is that viruses are about 125 nanometer in size and the carbanion atoms are only about 340 picometers. But specifically, COVID-19, also known as Coronavirus, is about 200 nanometer in size and the carbanion atoms are only about 340 picometers. The size difference is immense so that the carbanion can penetrate and invade the interior of the virus to kill it from the inside and attacking the vital points of a virus. The carbanion is a carbon atom in which contains a negative charge. The valence shell of a negatively charged carbon atom contains 8 electrons. Thus, its octet is complete, and it contains an extra pair of electrons for 8. The negatively charged carbon is in a state of sp3 hybridization. The hybrid orbitals are directed towards the corners of a tetrahedron. Three of the hybrid orbitals are involved in the formation of single covalent bonds with other atoms while the 5th hybrid orbital contains a lone pair of electrons. Thus, it has a pyramidal structure similar to NH3 molecule. The carbanion is a carbon that contains eight electrons which are highly reactive intermediate, and they are readily attacked by electrophilic reagents. Carbanion itself is a nucleophile.

The carbanions have had many successes throughout different viruses. The carbanions have been used in the past on many different people on many different viruses and have successfully treated the users.

The treatment using the carbanions has many testimonial occurrences that have fought off many different viruses. The occurrence is one of many cases where the patients were to use the carbanions with a nebulizer, three droplets a day for three days to treat COVID-19. It is also important to note that the carbanions are able to treat many different viruses due to similar structures since all viruses have similar structures as the carbanions are to enter the membrane of the virus to kill off vitals of the said virus. Some viruses in which was treated by the use of the carbanions are arenavirus, banana mild mosaic virus, banana virus, bean pod virus, echovirus, hantavirus, influenza virus, morbillivirus, mosaic cucumber mosaic virus, parainfluenza virus, paramyxovirus, parvovirus B19, poxvirus vaccinia virus, rhinovirus, soybean mosaic virus, banana streak virus, togavirus, varicella-zoster virus, and *Yersinia pestis* virus. Further, the carbanions may be used for treating diseases associated with different viruses.

Further, the present disclosure describes C-therapy to facilitates treating of cancer. Unlike traditional radiation, Carbon C- (carbanions) therapy targets cancer with 100 sextillion C-. Since their more exact, higher, and potentially more effective doses of radiation can be delivered, without causing damage to surrounding healthy tissues. C-therapy fights cancers and minimizes treatment side effects. Further C-therapy also facilitates treating prostate cancer, head and neck cancer, lung cancer, soft tissue cancer, pediatric cancer, breast cancer, etc.

Further, the present disclosure describes a compound that is used as a treatment for COVID-19 (coronavirus). Further, the compound may be an organic compound. Further, the compound is created by making use of the carbanion's physical chemistry. Further, the compound may be used for treating viral infections. Further, the compound is created by taking carbon atoms out of a plant and using temperature to create reduction or redox to add 2 electrons to the carbon atom generating the highly negatively charged organic carbon atoms. Further, the highly negatively charged organic carbon atoms puncture the membrane of the virus to release vital fluid which causes the virus to die.

Further, the present disclosure describes an organic compound that is used to treat and cure lung diseases caused by viruses, bacteria, or of the likes. Further, the present disclosure describes the use of carbanion's physical chemistry in the creation of a compound that is used as a lungs bacterial treatment for bacterial, fungus, virus, and diseases related to the lungs. Further, the highly negative charged organic carbon atoms of the organic compound puncture the membrane of the organism such as bacteria, fungi, etc.

Further, the present disclosure describes a compound that is used to treat and cure skin diseases. Further, the compound may be an organic compound. Further, the compound is created by making use of the carbanion's physical chemistry. Further, the compound may be used as a skin treatment/cure for skin diseases. Further, the compound is created by taking carbon atoms out of a plant and using temperature to create reduction or redox to add 2 electrons to the carbon atom generating the highly negatively charged organic carbon atoms. Further, the highly negative charged organic carbon atoms of the organic compound puncture the membrane of the organism such as bacteria, fungi, etc.

Further, the present disclosure relates to physical chemistry. Further, the present disclosure describes a method, process, and usage of creating a carbanion that is used as a treatment for contagious and/or infectious viruses.

Further, the present disclosure describes a treatment for contagious and infectious viruses. The present disclosure also describes a method and process of creating a carbanion as well as the unique usage of the carbanion as a treatment for contagious and/or infectious viruses. Furthermore, the present disclosure describes a cheap and cost-efficient treatment for contagious and/or infectious viruses. The present disclosure also describes a treatment to cure multiple known viruses and potentially undiscovered viruses.

FIG. 1 is a table 100 listing ingredients of a medicine composition for facilitating treating organs of a mammal, in accordance with some embodiments. Further, the table 100 may include a column 102 and two rows 104-106. Further, the table 100 may include two cells (column 102, row 104) and (column 102, row 106). Further, the medicine composition may include carbanions and a diluting agent.

Further, a cell (column 102, row 104) of the table 100 may be related to the carbanions. Further, a carbanion of the carbanions may include a carbon atom. Further, the carbon atom may include a formal charge of −1.

Further, a cell (column 102, row 106) of the table 100 may be related to the diluting agent. Further, the diluting agent may be capable of combining with the carbanions for forming at least one appliable form of the medicine composition. Further, the diluting agent may include at least one solvent. Further, the at least one solvent may include water, cream, oil, etc. Further, a ratio of the diluting agent to the carbanions by volume ranges from 512:1 to 32:1. Further, the combining facilitates applying of the at least one appliable form of the medicine composition to at least one organ of the mammal. Further, the at least one organ may include lungs, skin, etc. Further, the mammal may include a human. Further, the at least one appliable form of the medicine composition may include a solution, a suspension, an aerosol, an emulsion, etc.

Further, in some embodiments, the ratio of the diluting agent to the carbanions by the volume may be 284:1.

Further, in some embodiments, the ratio of the diluting agent to the carbanions by the volume may be 189:1.

Further, in some embodiments, the ratio of the diluting agent to the carbanions by the volume may be 57:1.

In further embodiment, the medicine composition may include an elemental composition in a ratio to the carbanions by volume. Further, the ratio of the elemental composition to the carbanions by the volume may be 1:9. Further, in an embodiment, the elemental composition may include oxygen, hydrogen, nitrogen, phosphorus, potassium, calcium, magnesium, sulfur, iron, silicon, aluminum, chlorine, and manganese.

Further, in some embodiments, each carbanion of the carbanions may be capable of creating an electromechanical reaction with an organic material of at least one organism present on the at least one organ of the mammal based on the applying of the at least one appliable form of the medicine composition. Further, the creating of the electromechanical reaction disassembles the organic material of the at least one organism for eliminating the at least one organism. Further, the eliminating of the at least one organism facilitates the treating of the at least one organ of the mammal. Further, the at least one organism may include viruses, bacteria, fungi, protozoa, insects, etc. Further, the insects may include pests, parasites, etc. Further, the organic material of the at least one organism may include lipid, protein, etc. Further, the at least one organism causes at least one disease to the at least one organ. Further, the at least one disease may include lung diseases, skin diseases, etc. Further, the lung diseases may include COVID-19. Further, the skin disease may include gangrene.

Further, in some embod

Further, the at least one disease causes degeneration of the at least one tissue of the at least one organ.

Further, in some embodiments, the at least one dosage of the at least one appliable form of the medicine composition may be associated with a dosing frequency. Further, the dosing frequency may include three times a day for at least one three days. Further, the applying of the at least one dosage of the at least one appliable form of the medicine composition with the dosing frequency facilitates the treating of the at least one organ.

Further, in some embodiments, the applying of the at least one appliable form of the medicine composition may be associated with an applying duration. Further, the at least one applying duration may include at least one minute, at least one hour, etc. Further, the treating of the at least one organ may be based on the applying of the at least one appliable form of the medicine composition for the applying duration.

Further, in some embodiments, the at least one appliable form of the medicine composition may include a solution. Further, the solution may be appliable to the at least one organ using at least one application method. Further, the at least one application method may include soaking, washing, inhaling, gargling, rinsing, etc. Further, the applying of the solution of the medicine composition to the at least one organ facilitates the treating of the at least one organ.

Figure 3:
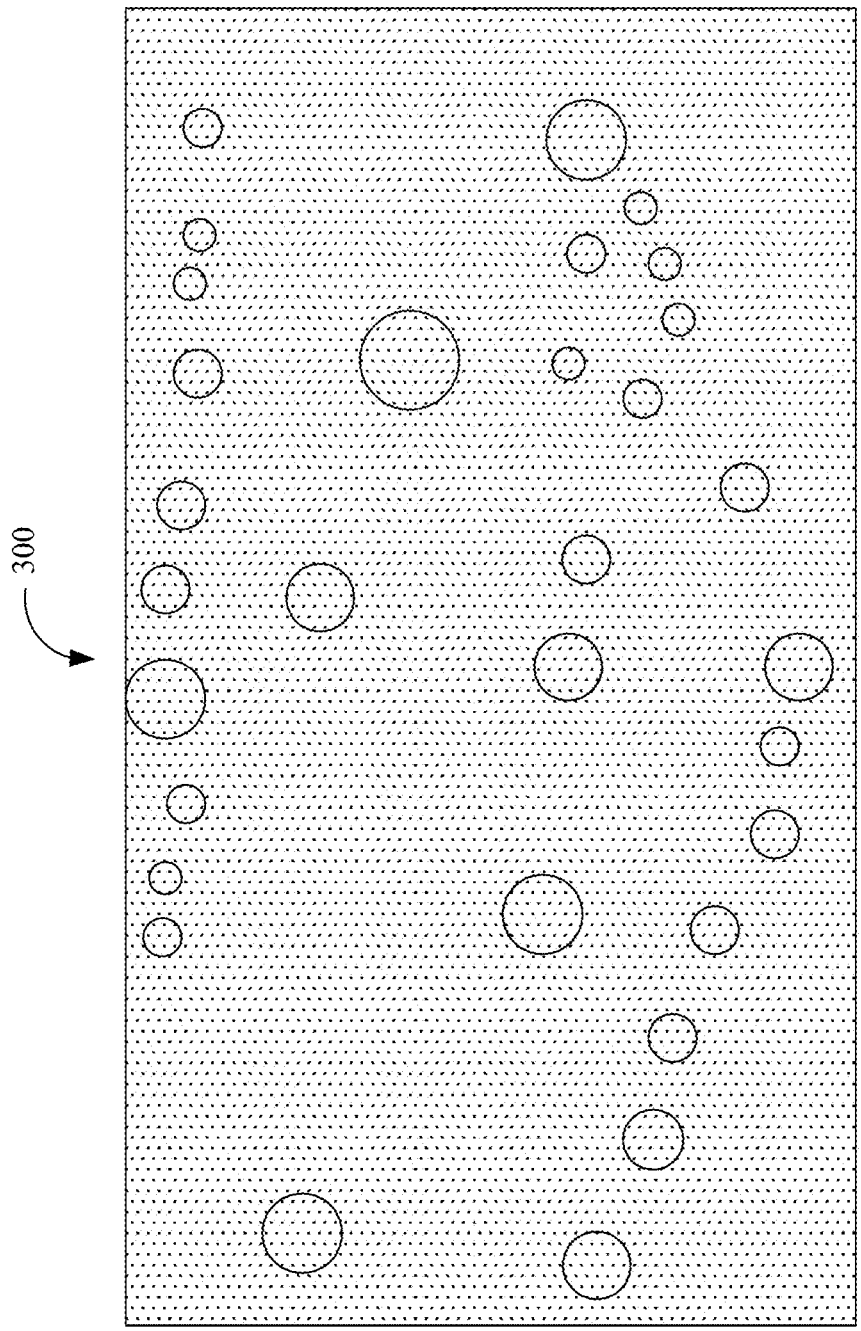
FIG. 3 is an illustration of carbanions of the medicine composition, in accordance with some embodiments.

FIG. 3 is an illustration of carbanions 300 of the medicine composition, in accordance with some embodiments. Further, the carbanions 300 may be derived from at least one organic material source. Further, the at least one organic material source may include at least one plant. Further, the carbanions 300 may include carbon atoms extracted from the at least one plant. Further, the carbanions 300 may include a 100% organic matter. Further, the organic matter may be organic carbon atoms. Further, at least one of a specific temperature and a specific pressure may be applied to the carbon atoms for initiating at least one of a reduction reaction and a redox reaction. Further, the at least one of the reduction reaction and the redox reaction adds 2 electrons to the carbon atoms for creating negatively charged carbon atoms. Further, each negatively charged carbon atom of the negatively charged carbon atoms may include 8 electrons and 6 protons, and 6 neutrons. Further, the negatively charged carbon atoms may be highly negatively charged. Further, the negatively charged carbon atoms may be the carbanions 300. Further, the carbanions 300 may include a trivalent carbon atom comprising eight (8) electrons in the valence shell of the trivalent carbon atom. Further, the carbanions 300 may be created using physical chemistry of the carbanions 300. Further, the carbanions 300 may include micelles structures. Further, the micelles structure may include a spherical shape.

Figure 4:
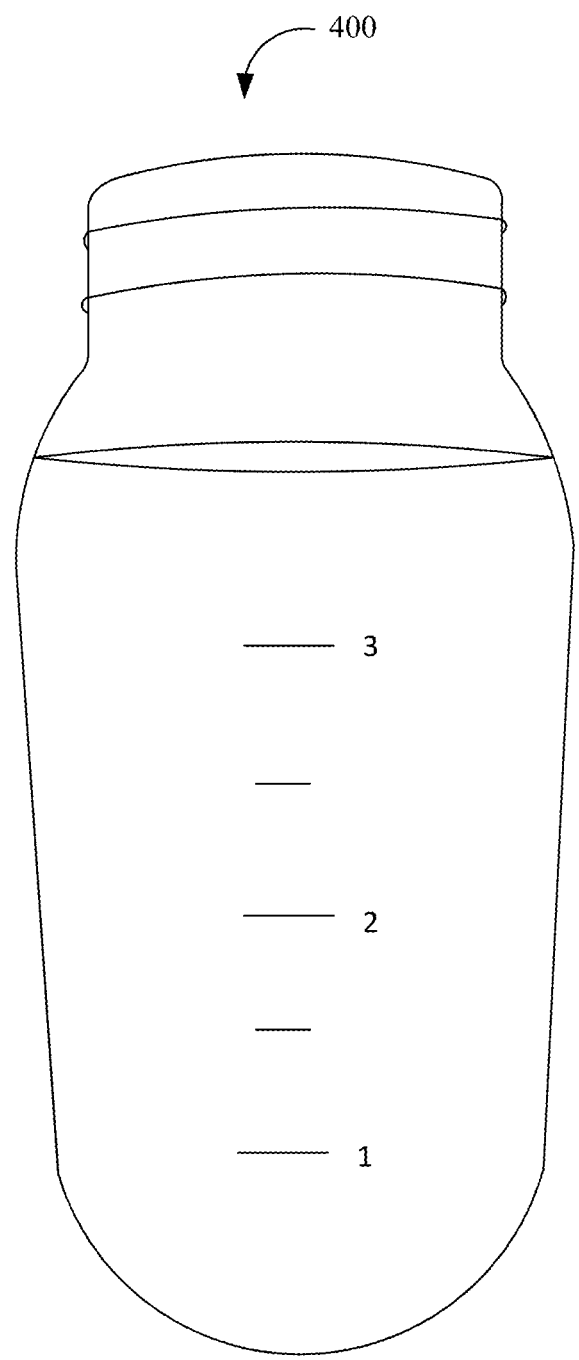
FIG. 4 is a front view of a container containing the medicine composition, in accordance with some embodiments.

FIG. 4 is a front view of a container 400 containing the medicine composition, in accordance with some embodiments. Further, the medicine composition may include the carbanions and the diluting agent. Further, the medicine composition may be configured for treating the organs of the mammal. Further, the organs may have at least one disease. Further, the treating may include curing the at least one disease associated with the organs. Further, the organs may include lungs, skin, etc. of the mammal. Further, the mammal may include a human and an animal. Further, the at least one disease may include lung diseases, skin diseases, etc. Further, the lung diseases may include COVID-19. Further, the skin diseases may include gangrene. Further, at least one of fungi, bacteria, viruses, and insects may cause the at least one disease. Further, the insects may include pests, parasites, etc. Further, the carbanions may be derived from at least one organic source. Further, the at least one organic source may include at least one plant. Further, the carbanions may include 100% organic matter. Further, the organic matter may include organic carbon atoms. Further, the carbanions may include carbon atoms. Further, the carbon atoms may be extracted from the at least one plant. Further, at least one of a specific temperature and a specific pressure may be applied to the carbon atoms for initiating at least one of a reduction reaction and a redox reaction. Further, the initiating of the at least one of the reduction reaction and the redox reaction may add 2 electrons to the carbon atoms creating negatively charged carbon atoms. Further, each negatively charged carbon atom of the negatively charged carbon atoms may include 8 electrons and 6 protons, and 6 neutrons. Further, the negatively charged carbon atoms may be highly negatively charged. Further, the negatively charged carbon atoms may be the carbanions. Further, the carbanions may include a trivalent carbon atom comprising eight (8) electrons in the valence shell of the trivalent carbon atom. Further, the negatively charged carbon atoms may be created using the physical chemistry of the carbanions. Further, the negatively charged carbon atoms may be configured for puncturing the membrane of the at least one of the fungi, the bacteria, the viruses, and the insects. Further, the puncturing of the membrane makes the at least one of the fungi, the bacteria, the viruses, and the insects may eliminate the at least one of the fungi, the bacteria, the viruses, and the insects. Further, the puncturing of the membrane makes the at least one of the fungi, the bacteria, the viruses, and the insects inactive and facilitates treating the organs.

Further, in some embodiments, the puncturing of the membrane of the at least one of the fungi, the bacteria, the viruses, and the insects may release vital fluids of the at least one of the fungi, the bacteria, the viruses, and the insects. Further, the release of the vital fluids may cause the death of the at least one of the fungi, the bacteria, the viruses, and the insects making the at least one of the fungi, the bacteria, the viruses, and the insects inactive. Further, the death of the at least one of the fungi, the bacteria, the viruses, and the insects may facilitate the treating of the organs.

Further, in some embodiments, the at least one disease may include bacterial diseases associated with the bacteria. Further, the organs may have the bacterial diseases Further, the bacterial diseases may include Bronchitis, Chronic Cough, Common Cold, Influenza, Pertussis, Pleurisy, Pneumonia, Sarcoidosis, Spirometry, Sudden Infant Death Syndrome (SIDS), Tuberculosis, actinomycosis, Anthrax, boutonneuse fever, brucellosis, brucellosis spondylitis, campylobacteriosis, Carrion disease, cat scratch disease, cervicitis, chancroid, chlamydia, lymphogranuloma venereum, cholera, clostridial infection, dysentery, shigellosis, epididymitis, erysipelothrix infection, glanders, gonorrhea, granuloma inguinale, Legionnaire disease, Leprosy, leptospirosis, listeriosis, Lyme disease, Melioidosis, nocardiosis, paratyphoid fever, pharyngitis, plague, bubonic plague, pneumonia, proctitis, pseudotuberculosis, psittacosis, Q fever, rat-bite fever, Reiter syndrome, relapsing fever, rheumatic fever, Rocky Mountain spotted fever, Salmonellosis, scarlet fever, septicemia, Waterhouse-Friderichsen syndrome, Shigellosis, streptobacillary fever, syphilis, bejel, gumma, yaws, tetanus, tonsillitis, toxic shock syndrome, trench fever, tuberculosis, scrofula, tularemia, typhoid fever, typhus, scrub typhus, urethritis, vaginitis, vesiculitis, vulvitis, whooping cough, yersiniosis, etc.

Further, in some embodiments, the at least one disease may include fungal diseases associated with the fungi.

Further, the organs may have the fungal diseases. Further, the fungal diseases may include Aspergillosis, Cryptococcosis, Candidiasis, Mucormycosis, *Pneumocystis jirovecii* Pneumonia, aspergillosis, Blastomycosis, candidiasis, thrush, chromoblastomycosis, coccidioidomycosis, cryptococcosis, histoplasmosis, pharyngitis, pneumonia, sporotrichosis, urethritis, vaginitis, vulvitis, etc.

Further, in some embodiments, the at least one disease may include protozoa diseases associated with protozoa. Further, the organs may have the protozoa diseases. Further, the protozoa diseases may include avian malaria, Chagas disease, Coccidiosis, leishmaniasis, Oriental sore, Malaria, blackwater fever, sleeping sickness, toxoplasmosis, trichomoniasis, trypanosomiasis, etc Further, in some embodiments, the treating of the lungs and the curing of the lung diseases may include an application of the medicine composition to the lungs. Further, the application may include at least one of inhaling, gargling, drinking, etc. Further, the application may be associated with at least one duration. Further, the at least one duration may include at least one second, at least one minute, at least one hour, etc. Further, the application may be repeated after at least one second duration of at least one first duration. Further, the at least one first duration may include at least one first minute, at least one first hour, at least one first day. Further, the at least one second duration may include at least one second minute, at least one second hour, at least one second day. Further, in an embodiment, the application may include at least three applications in a day for three days. Further, each application of the at least three applications may include a dosage of the carbanions. Further, the dosage may include 2 to 10 drops. Further, 1 drop may include 5 sextillion carbanions. Further, the 2-10 drops may include 10 to 50 sextillion carbanions.

Further, in some embodiments, the medicine composition may be administered using a nebulizer. Further, the nebulizer may use a solution of the medicine composition. Further, the solution may include at least three drops of the carbanions mixed with an ounce of the water. Further, the nebulizer may turn the solution into a mist for inhaling the solution. Further, the at least one of the humans and the animals may inhale the mist. Further, the inhaling of the mist may facilitate the treating of the organs and the curing of the diseases. Further, the inhaling of the solution three times a day for at least three days facilitate the treating and the curing. Further, one drop of the carbanions may include 5 sextillion carbon atoms. Further, one ounce may include 353 drops.

Further, in some embodiments, the treating of the skin and the curing of the skin diseases may include an application of the medicine composition on the skin. Further, the application may include at least one of rubbing, massaging, coating, soaking, washing, spraying, etc. Further, the application may be associated with at least one duration. Further, the at least one duration may include at least one second, at least one minute, at least one hour, etc. Further, the application may be repeated after at least one second duration of at least one first duration. Further, the at least one first duration may include at least one first minute, at least one first hour, at least one first day. Further, the at least one second duration may include at least one second minute, at least one second hour, at least one second day.

Further, in some embodiments, the treating of the skin and the curing of the skin diseases may include regenerating the skin of at least one body part of the human. Further, the at least one of the treating and the curing may include growing of the skin on the at least one body part.

Further, in some embodiments, the skin diseases may be associated with skin conditions of the skin. Further, the skin conditions may include burns, acne, infections of the skin. Further, a PicoSkin comprising the medicine composition may be used to prevent infection in second and third-degree burns. Further, PicoSkin may be sprayed on the burns affected areas of the skin multiple times per day. Further, the PicoSkin may be applied on the acne-affected areas of the skin. Further, the PicoSkin may reduce skin oil and kill infections. Further, the infection on the skin may include bacterial infections, fungal infections, yeast, viral, Ricketsial, and chemical burns. Further, the PicoSkin may cure the infection on the skin.

Further, in some embodiments, the medicine composition may be used in a cream. Further, the cream may be applied twice a day for two days. Further, the cream may include Shea butter. Further, twice the day may include a morning time and a bed time. Further, each of the morning time and the bed time may be associated with a dosage of the carbanions. Further, the dosage may include ⅓ oz. Further, 1 oz may include 353 drops. Further, the ⅓ oz may be 118 drops. Further, 1 drop may include 5 sextillion carbanions. Further, the 118 drops may include 590 sextillion carbanions.

Further, in some embodiments, a "Pico Skin Relief" comprising the medicine composition. Further, the "Pico Skin Relief" may be a 100% concentrate in liquid or cream. Further, the "Pico Skin Relief" may be a 100% concentrate made of US Government FDA EAFUS food additives. Further, the "Pico Skin Relief" may be like a single element, not a chemical compound. Further, the "Pico Skin Relief" may be safe for ingestion and inhalation. Further, the "Pico Skin Relief" may be applied to the internal and external skin of the at least one body part. Further, the "Pico Skin Relief" may be cosmetic moisturizer for skin issues of debriding, cleansing wash, to promote healing and or pain relief. Further, the "Pico Skin Relief" may be used for skin issues of skin softening, bio-films, crust, scab, divots, fungal, molds, sun-spots, granules, inflammation, lesions, ulcers, itchy, skin loss, oozing, sores, wounds, pigment changes, pimples, rashes, scabbing, shards, leathery skin, callus, and dry skin. Also, it helps with skin sensations of biting, burning, crawling, creeping, itching, pricking, pinching, and stinging. Further, the "Pico Skin Relief" may be available as a liquid or cream product.

Further, in an embodiment, the skin diseases may include Genetic Blistering, Dog Ear Infection, Lamb Gangrene Infection, MRSA, Psoriasis, Squamous Cancer, Arm Dandruff, Ringworms, Whooping Cough Pneumonia, Parasite Scabies, Basal Cell Cyst, Cellulitis, Head Lice, Lupus, etc. Further, the "Pico Skin Relief" may facilitate the treating of the skin and the curing of the skin diseases.

Further, in an embodiment, the skin diseases may include gangrene. Further, the gangrene may be associated with the at least one body part. Further, the gangrene may be a potentially life-threatening condition that arises when a considerable mass of body tissue dies (necrosis). Further, the gangrene may occur after an injury or infection, or in people suffering from any chronic health problem affecting blood circulation. Further, the primary cause of gangrene may be reduced blood supply to the affected tissues, which results in cell death. Further, the gangrene may be caused by ischemia or infection, such as by the bacteria *Clostridium perfringens* or by thrombosis (a blood vessel blocked by a blood clot). Further, the gangrene may be usually the result of critically insufficient blood supply (e.g., peripheral vascular disease) and may be often associated with diabetes and long-term tobacco smoking. Further, the gangrene may be most common in the lower extremities (such as the leg). The best medical treatment today for the gangrene may be revascularization (i.e., restoration of blood flow) of the afflicted organ, which can reverse some of the effects of necrosis and allow healing. Further, the other treatment of the gangrene may include debridement and surgical amputation. Further, the method of treatment may be generally determined by the location of affected tissue and the extent of tissue loss.

Further, the treatment of the gangrene may include applying a moisturizer. Further, the moisturizer may be made up of 90% of 600 (Pico meter) carbon particles. Further, the treatment may eliminate the gangrene. Further, the treatment may eliminate the wound of the gangrene. Further, the treatment may make the skin grow from the edges to the center of the gangrene wound. Further, the treatment may cure the gangrene without the reduction of body parts affected by the gangrene. Further, the gangrene may cause the Gangrene Black on the body parts. Further, the application of "Pico Skin Relief" may remove the Gangrene Black. Further, the "Pico Skin Relief" may include the carbanions. Further, the application of the "Pico Skin Relief" starts the process of skin growth on the body parts. Further, the application of the "Pico Skin Relief" for at least three days may cause a 100% reduction in the black Gangrene part on foot. Further, the application of the "Pico Skin Relief" may cause growth in the tissue on an upper part of the foot. Further, the application of the "Pico Skin Relief" may cause the skin to grow and reverse the damage caused by the gangrene on the foot. Further, the application of the "Pico Skin Relief" may include 4 oz per gallon dilution. Further, the application may include three foot-baths daily for 30 min. Further, the application may cause the forming of tan-colored covering. Further, the tan-colored forming may be mucoid exudate that forms on the healing of a full thickness wound of the gangrene. Further, skin form over an entire surface at one time other than skin cells being sprayed onto a matrix placed on a skinless wound. Further, the "Pico Skin Relief" may replace the traditional treatment of the gangrene. Further, the traditional treatment may include surgical debridement, wound care, and antibiotic therapy, and amputation is necessary in many cases. Further, the amputation may be performed for an ischemic disease of the lower extremity. Of dysvascular amputations, 15-28% of patients undergo contralateral limb amputations within 3 years. Of elderly persons who undergo amputations, 50% survive the first 3 years. Further, the treatment using the "Pico Skin Relief" may cure the gangrene without performing the amputation.

Further, the "Pico Skin Relief" may be used for treating the gangrene. Further, the treating may eliminate the gangrene without the amputation of the affected body part (such as legs). Further, the "Pico Skin Relief" may be used in 4 oz per gallon dilution. Further, the treating of the gangrene may include at least three applications of the "Pico Skin Relief" to the leg for at least thirty minutes. Further, the treating of the gangrene may include removal of gangrene black of the leg, growth in the skin of the leg, and formation of tissue on the leg.

Further, in some embodiments, the carbanions may control gram-positive bacteria at 16,000 of the water to 1. Further, the carbanions may control the gram-positive bacteria at 1 ml to 16 liters of water.

Further, in some embodiments, a carbanion of the carbanions may be an anion in which carbon bears a formal negative charge. Further, the carbanion may include eight electrons in the valence shell of the carbon. Further, a carbon-atom of the carbanion may include a negative charge. Further, the valence shell of a negatively charged carbon atom may include 8-electrons. Further, the octet of the negatively charged carbon atom may be complete. Further, the negatively charged carbon atom may include an extra pair of electrons. Further, the negatively charged carbon atom may be in a state of sp3 hybridization. Further, the hybrid orbitals may be directed towards the corners of a tetrahedron. Further, three hybrid orbitals may be involved in the formation of single covalent bonds with other atoms while the fourth hybrid orbital may include a lone pair of electrons. Further, the carbanion may include a pyramidal structure similar to NH3 (Ammonia) molecule. Further, the carbon-atom may include eight electrons. Further, the carbon-atom may be a highly reactive intermediate. Further, the carbon-atom may be readily attacked by electrophilic reagents. Further, the carbanion may be a nucleophile.

Further, the carbanion may include "Negative Octet Energy". Further, the carbanion may be an anion in which the carbon-atom bears a formal negative charge. Further, in an embodiment, the carbanion may include a single negatively charged carbon atom. Further, the single negatively charged carbon atom bonds to no other atoms except for another single negatively charged carbon atom.

Figure 5:
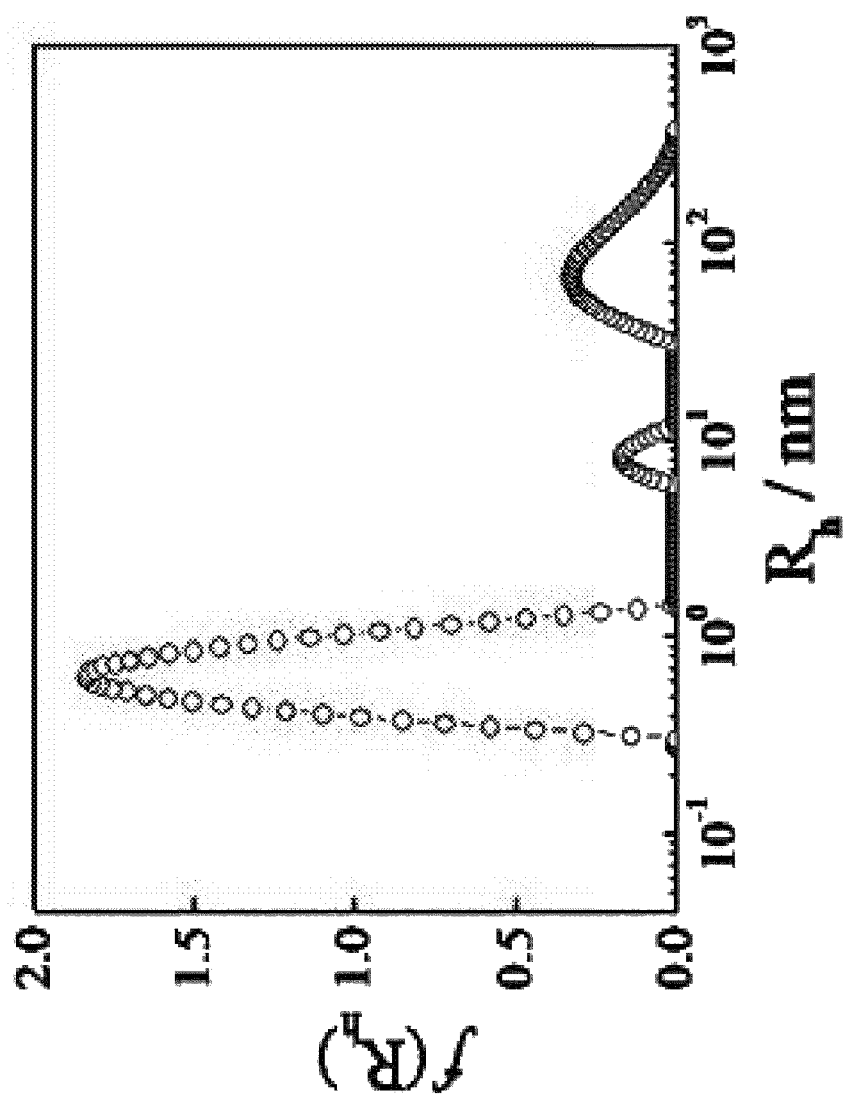
FIG. 5 is a plot of light scattering by the carbanions through a dynamic light scattering, in accordance with some embodiments.

FIG. 5 is a plot of light scattering by the carbanions through a dynamic light scattering, in accordance with some embodiments. Further, the dynamic light scattering may be a technique for measuring a particle size. Further, the particle size range from a few nanometers (nm) to a few microns. Further, the light intensity may be proportional to the size of "aggregates". Further, the dynamic light scattering may be an excellent tool for translocation. Further, 0.6 nm peaks may show greater intensity-weight distribution. Further, large aggregates scatter the storing light for 0.6 nm peak. Further, most micelles may be 0.6 nm in particle size hydrodynamic radius.

Figure 6:
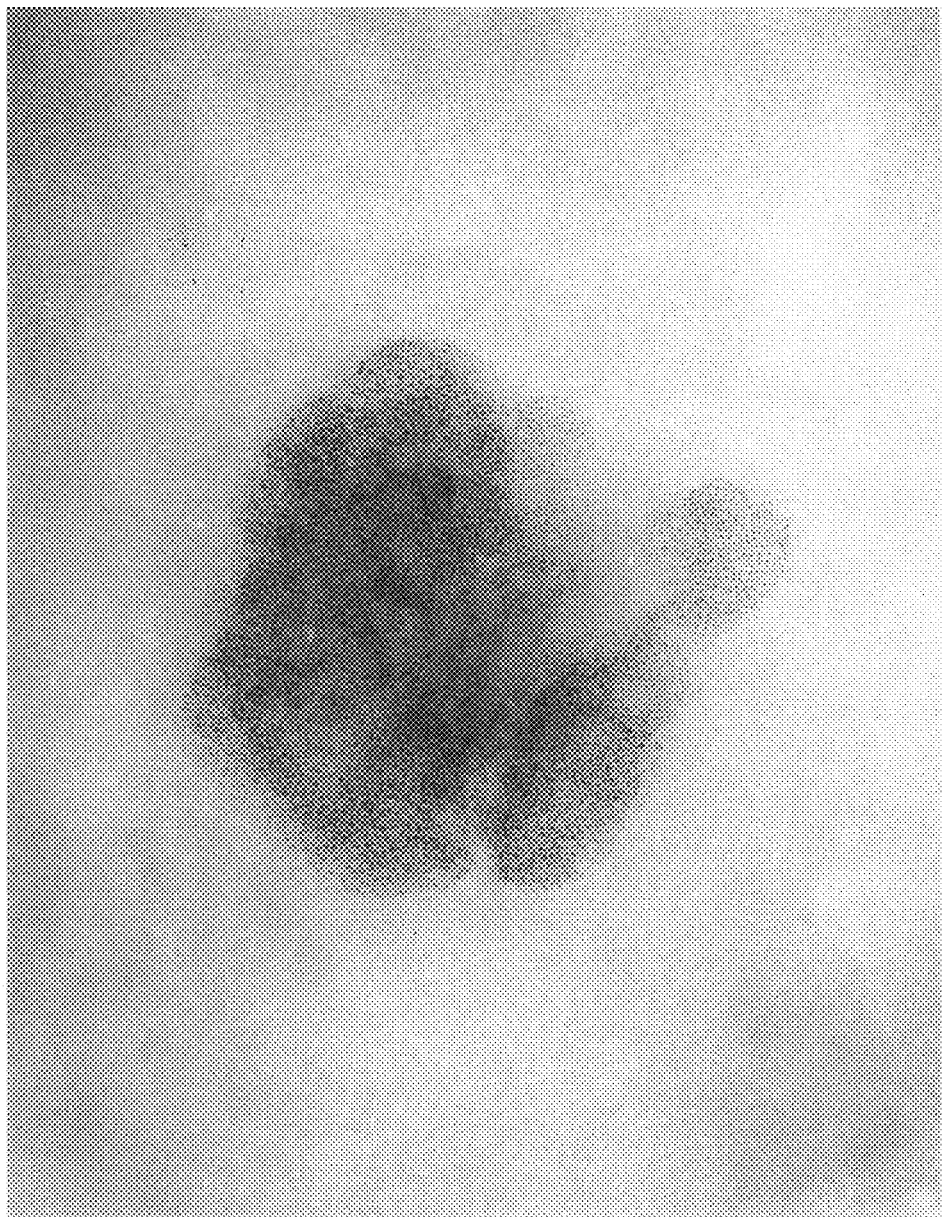
FIG. 6 is a magnified view of a sample of a solution of the medicine composition, in accordance with some embodiments.

FIG. 6 is a magnified view of a sample of a solution of the medicine composition, in accordance with some embodiments. Further, the solution may include a 1:1 dilution. Further, the sample of the solution may be magnified up to 100,000×. Further, the sample of the solution may include droplets with small grains. Further, the droplets may include the carbanions.

Figure 7:
FIG. 7 is a magnified view of a sample of the solution, in accordance with some embodiments.

FIG. 7 is a magnified view of a sample of the solution, in accordance with some embodiments. Further, the solution may include a 1:1 dilution. Further, the sample of the solution may be magnified up to 100,000×. Further, the sample of the solution may include droplets with small grains. Further, the droplets may include the carbanions.

Figure 8:
FIG. 8 is a magnified view of a sample of a solution of the medicine composition, in accordance with some embodiments.

FIG. 8 is a magnified view of a sample of a solution of the medicine composition, in accordance with some embodiments. Further, the solution may include a 1:100 dilution. Further, the sample of the solution may be magnified up to 100,000×. Further, the sample of the solution may include droplets with small grains. Further, the droplets may include the carbanions.

Figure 9:
FIG. 9 is a magnified view of a sample of the solution, in accordance with some embodiments.

FIG. 9 is a magnified view of a sample of the solution, in accordance with some embodiments. Further, the solution may include a 1:100 dilution. Further, the sample of the solution may be magnified up to 100,000×. Further, the sample of the solution may include droplets with small grains. Further, the droplets may include the carbanions.

Figure 10:
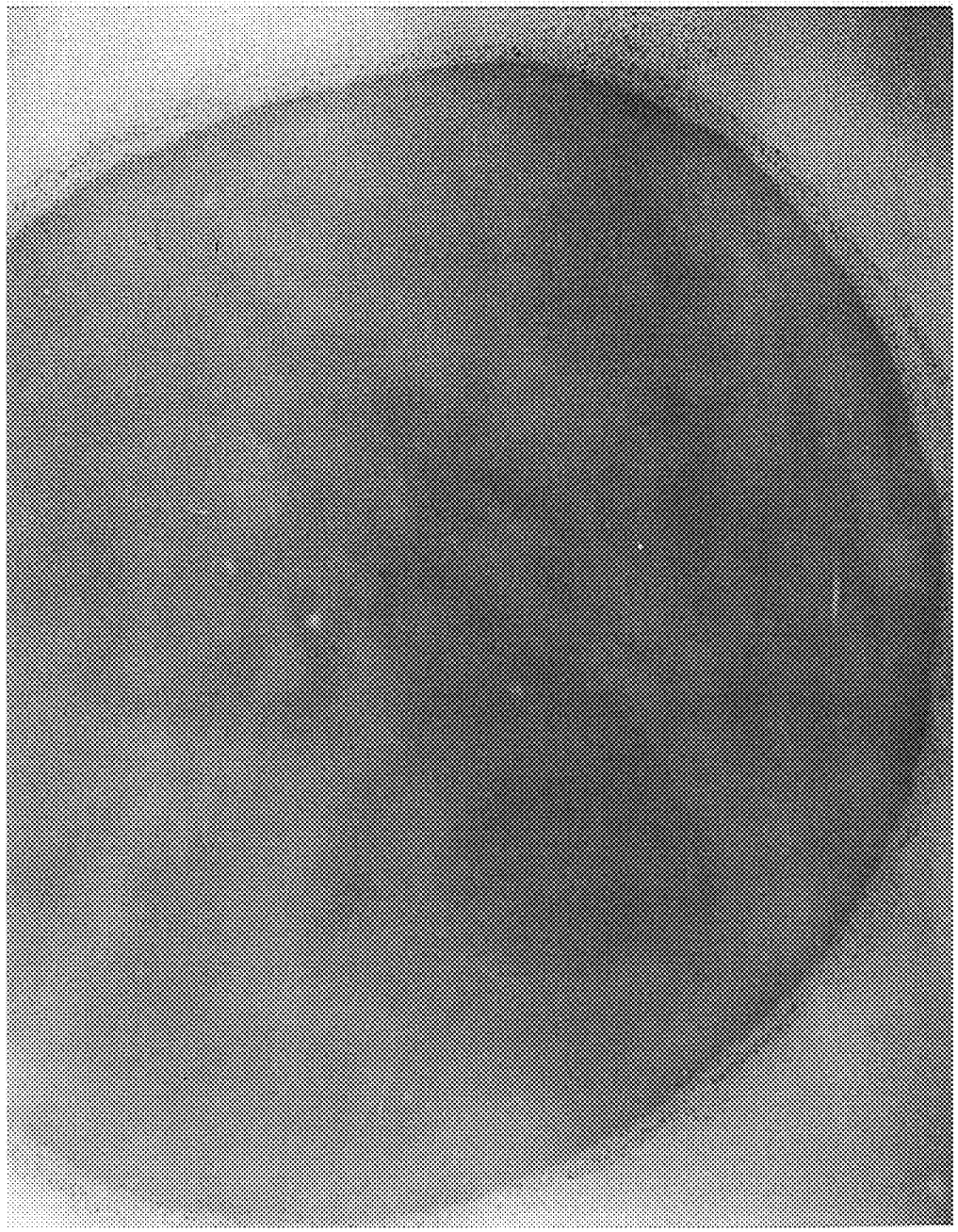
FIG. 10 is a magnified view of a sample of a solution of the medicine composition, in accordance with some embodiments.

FIG. 10 is a magnified view of a sample of a solution of the medicine composition, in accordance with some embodiments. Further, the solution may include a straight solution. Further, the solution may be magnified up to 100,000×. Further, the sample of the solution may include droplets.

Further, the droplets may include similar size particles around the edges, but inside, the grain is less than 1 nm (nanometer). Further, the droplets may include the carbanions.

Figure 11:
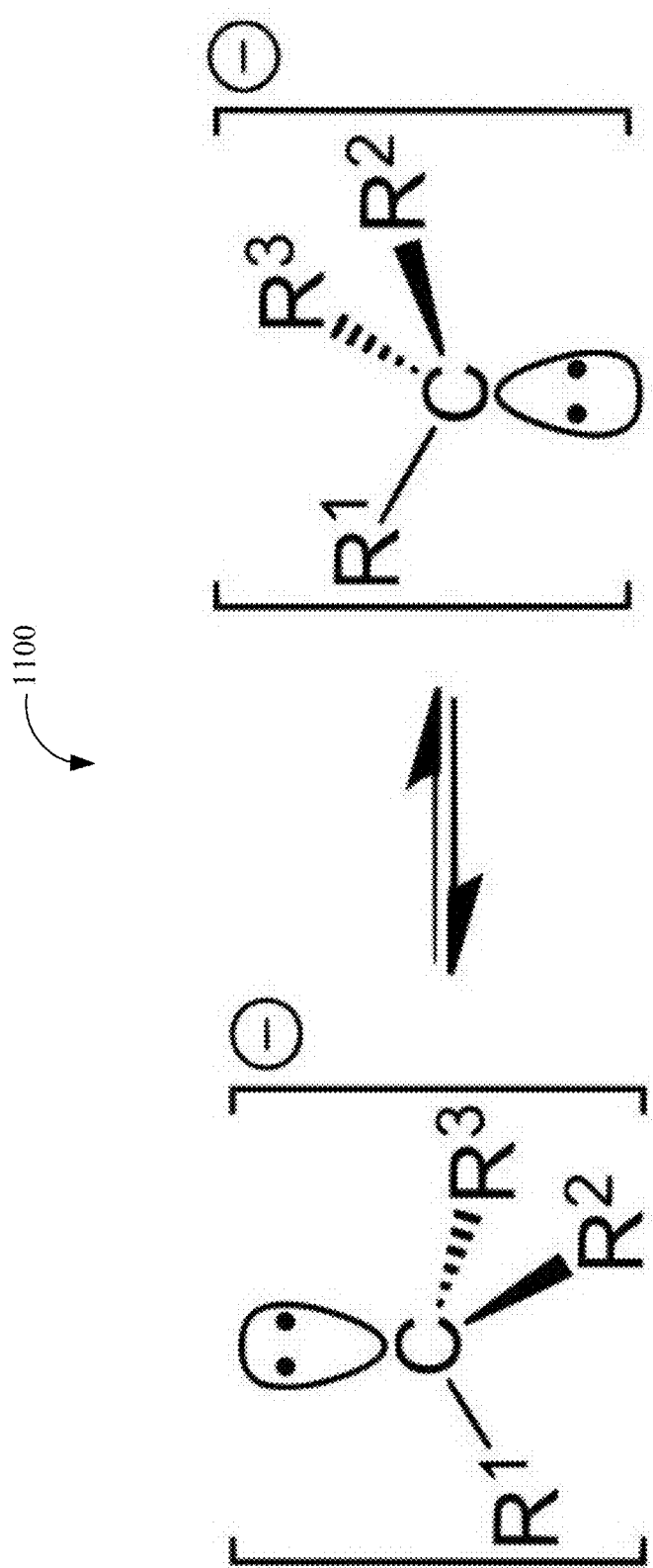
FIG. 11 is a schematic of a carbanion of the carbanions, in accordance with some embodiments.

FIG. 11 is a schematic of a carbanion 1100 of the carbanions, in accordance with some embodiments. Further, the carbanion 1100 is an anion in which carbon bears a formal negative charge. Further, the carbanion 1100 may include eight electrons in the valence shell of the carbon. Further, a carbon-atom of the carbanion 1100 may include a negative charge. Further, the valence shell of a negatively charged carbon-atom may include 8-electrons. Further, the octet of the negatively charged carbon atom may be complete. Further, the negatively charged carbon atom may include an extra pair of electrons. Further, the negatively charged carbon may be in a state of sp3 hybridization. Further, the hybrid orbitals may be directed towards the corners of a tetrahedron. Further, three of the hybrid orbitals may be involved in the formation of single covalent bonds with other atoms while the fourth hybrid orbital may include a lone pair of electrons. Further, the carbanion 1100 may include a pyramidal structure similar to NH3 molecule. Further, the carbon-atom may include eight electrons even the carbon-atom may be a highly reactive intermediate. Further, the carbon-atom may be readily attacked by electrophilic reagents. Further, the carbanion 1100 may be a nucleophile.

Figure 12:
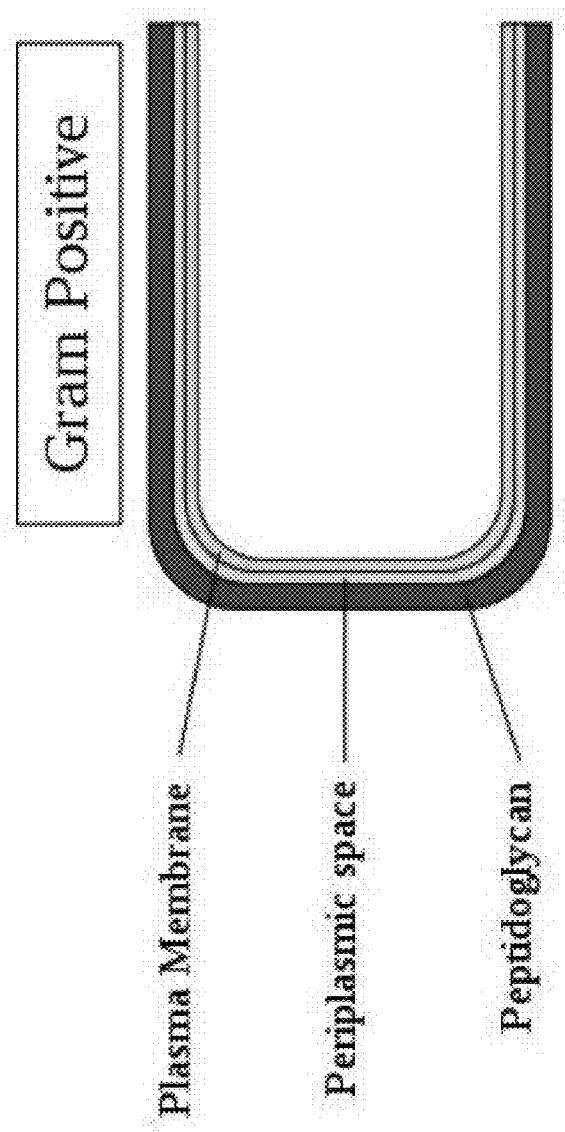
FIG. 12 is an illustration of gram-positive bacteria.

FIG. 12 is an illustration of gram-positive bacteria. Further, the gram-positive bacteria retain crystal violet dye and stain dark violet or purple. Further, the gram-positive bacteria remain blue or purple colored with gram stain when washed with absolute alcohol and water. Further, the gram-positive bacteria may include a thick (multilayered) Peptidoglycan layer. Further, Teichoic acids may be present in most of the gram-positive bacteria. Further, Periplasmic space is absent in the gram-positive bacteria. Further, an outer membrane is absent in the gram-positive bacteria. Further, Lipopolysaccharide (LPS) content is virtually absent in the gram-positive bacteria. Further, the gram-positive bacteria may include low Lipid and lipoprotein content. Further, acid-fast bacteria may have lipids linked to peptidoglycan. Further, the gram-positive bacteria may primarily produce Exotoxins. Further, a flagellar structure of the gram-positive bacteria may include 2 rings in the basal body. Further, the gram-positive bacteria may have high resistance to physical disruption. Further, the gram-positive bacteria may have high inhibition by basic dyes. Further, the gram-positive bacteria may have a high susceptibility to anionic detergents. Further, the gram-positive bacteria may have high resistance to sodium azide. Further, the gram-positive bacteria may have high resistance to drying. Further, the cell wall of the gram-positive bacteria is 100-120 Å thick and single-layered. The lipid content of the cell wall is low, whereas Murein content is 70-80% (higher). Further, Mesosome is more prominent in the gram-positive bacteria. Further, the gram-positive bacteria are more susceptible to antibiotics.

Figure 13:
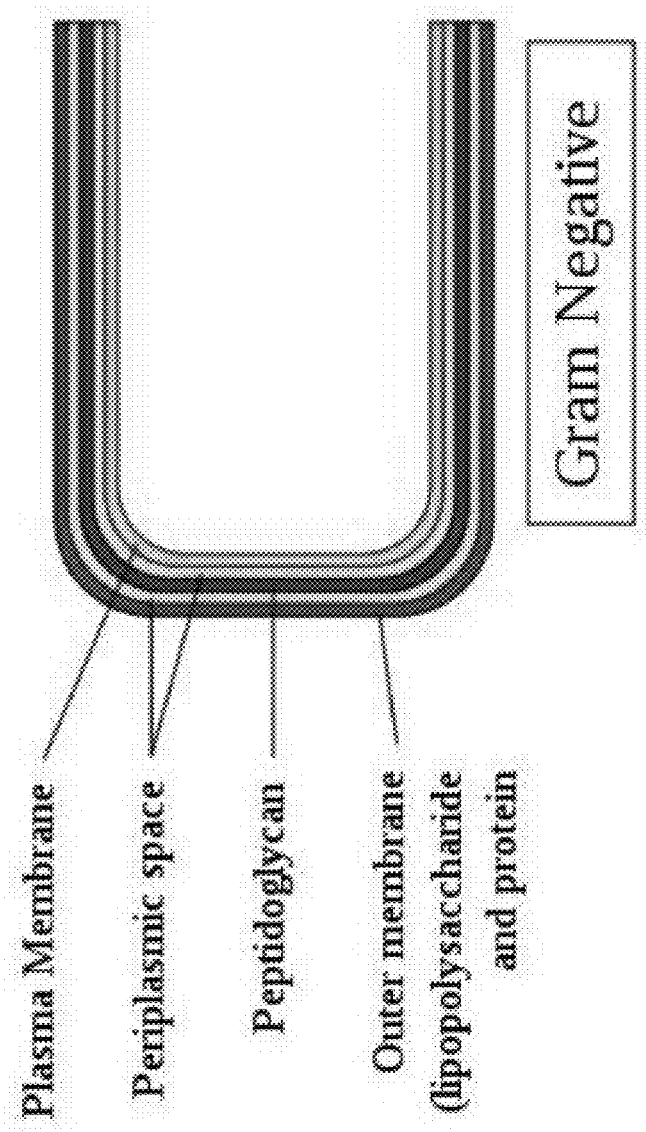
FIG. 13 is an illustration of gram-negative bacteria.

FIG. 13 is an illustration of gram-negative bacteria. Further, the gram-negative bacteria may be decolorized to accept counterstain (Safranin or Fuchsine) to stain red or pink. Further, the gram-negative bacteria do not retain the Gram stain when washed with absolute alcohol and acetone. Further, the gram-negative bacteria may include a thin (single-layered) Peptidoglycan layer. Further, Teichoic acids are absent in most of the gram-negative bacteria. Further, Periplasmic space is present in gram-negative bacteria. Further, an outer membrane is present in the gram-negative bacteria. Further, Lipopolysaccharide (LPS) content is high in the gram-negative bacteria. Further, the gram-negative bacteria may include a high lipid and lipoprotein content due to the presence of the outer membrane. Further, the gram-negative bacteria may primarily produce Endotoxins. Further, a flagellar structure of the gram-negative bacteria may include 4 rings in the basal body. Further, the gram-negative bacteria may have a low resistance to physical disruption. Further, the gram-negative bacteria may have low inhibition by basic dyes. Further, the gram-negative bacteria may have low susceptibility to anionic detergents. Further, the gram-negative bacteria may have a low resistance to sodium azide. Further, the gram-negative bacteria may have a low resistance to drying. Further, the cell wall of the gram-negative bacteria is 70-120 Å (ångström) thick and two-layered. Further, Lipid content is 20-30% (high) and Murein content is 10-20% (low). Further, Mesosome is less prominent in the gram-negative bacteria. Further, the gram-negative bacteria are more resistant to antibiotics.

Further, the gram-positive bacteria and the gram-negative bacteria are differentiated based on the structural differences in cell walls of the gram-positive bacteria and the gram-negative bacteria. Gram-positive bacteria retain the crystal violet dye do so because of a thick layer of peptidoglycan. In contrast, Gram-negative bacteria do not retain the violet dye and are colored red or pink. Compared with Gram-positive bacteria, Gram-negative bacteria are more resistant against antibodies because of the impenetrable cell wall. Further, the gram-positive bacteria and the gram-negative bacteria have a wide variety of applications ranging from medical treatment to industrial use and Swiss cheese production.

Further, the microscopic view of dental plaque shows Gram-positive bacteria (purple) and gram-negative bacteria (red). Further, in a Gram stain test, the gram-positive bacteria and the gram-negative bacteria are washed with a decolorizing solution after being dyed with crystal violet. On adding a counterstain such as safranin or fuchsine after washing, Gram-negative bacteria are stained red or pink while Gram-positive bacteria retain crystal violet dye. This is due to the difference in the structure of the bacterial cell wall of the gram-positive bacteria and the gram-negative bacteria. Gram-positive bacteria do not have an outer cell membrane found in Gram-negative bacteria. The cell wall of Gram-positive bacteria is high in peptidoglycan which is responsible for retaining the crystal violet dye.

Further, both gram-positive bacteria and gram-negative bacteria may be pathogenic. Further, six gram-positive genera of bacteria are known to cause disease in humans: *Streptococcus, Staphylococcus, Corynebacterium, Listeria, Bacillus*, and *Clostridium*. Another three cause diseases in plants: *Rathybacter, Leifsonia*, and *Clavibacter*. Many gram-negative bacteria are also pathogenic e.g., *Pseudomonas aeruginosa, Neisseria gonorrhoeae, Chlamydia trachomatis*, and *Yersinia pestis*. Gram-negative bacteria are also more resistant to antibiotics because the outer membrane may include a complex lipopolysaccharide (LPS) whose lipid portion acts as an endotoxin.

Further, a lot of Gram-negative bacteria are resistant to a number of important antibiotics that are used to treat the gram-negative bacteria. Further, agents like *Acinetobacter, Pseudomonas, E. coli*. Further, the gram-negative bacteria have very quickly developed resistance to antibiotics. Gram-negative agents becoming very rapidly more and more resistant to all of the agents. Greater resistance of gram-negative bacteria also applies to a newly discovered class of antibiotics. Further, the drugs are not likely to work on gram-negative bacteria. Further, bacteria are classified based on the cell shape into bacilli (rod-shaped) and cocci (sphere-shaped). Typical Gram-positive cocci stains include Clusters: usually characteristic of *Staphylococcus*, such as *S. aureus*, Chain: usually characteristic of *Streptococcus*, such as *S. pneumoniae*, B group streptococci, Tetrad: usually characteristic of *Micrococcus*.

Further, gram-positive bacilli tend to be thick, thin, or branching.

Further, many streptococcal species are nonpathogenic and form part of the commensal human microbiome of the mouth, skin, intestine, and upper respiratory tract. Further, the streptococcal species is also a necessary ingredient in producing Emmentaler (Swiss) cheese. Non-pathogenic species of *corynebacterium* are used in the industrial production of amino acids, nucleotides, bioconversion of steroids, degradation of hydrocarbons, cheese aging, production of enzymes, etc. Many *Bacillus* species are able to secrete large quantities of enzymes. *Bacillus amyloliquefaciens* is the source of a natural antibiotic protein barnase (a ribonuclease), alpha amylase used in starch hydrolysis, the protease subtilisin used with detergents, and the BamH1 restriction enzyme used in DNA research. *C. thermocellum* may utilize lignocellulose waste and generate ethanol, thus making it a possible candidate for use in the production of ethanol fuel. It is anaerobic and is thermophilic, which reduces cooling costs. *C. acetobutylicum*, also known as the Weizmann organism, was first used by Chaim Weizmann to produce acetone and biobutanol from starch in 1916 for the production of gunpowder and TNT. *C. botulinum* produces a potentially lethal neurotoxin that is used in a diluted form in the drug Botox. It is also used to treat spasmodic torticollis and provides relief for approximately 12 to 16 weeks. The anaerobic bacterium *C. ljungdahlii* may produce ethanol from single-carbon sources including synthesis gas, a mixture of carbon monoxide, and hydrogen that may be generated from the partial combustion of either fossil fuels or biomass. Gram-indeterminate and Gram-variable Bacteria Not all bacteria may be reliably classified through Gram staining. For example, acid-fast bacteria or Gram-variable do not respond to Gram staining.

Figure 14:
FIG. 14 is an illustration of an effect of NG 1 on *Alternaria alternata*, in accordance with some embodiments.

FIG. 14 is an illustration of an effect of NG 1 on *Alternaria alternata*, in accordance with some embodiments.

Figure 15:
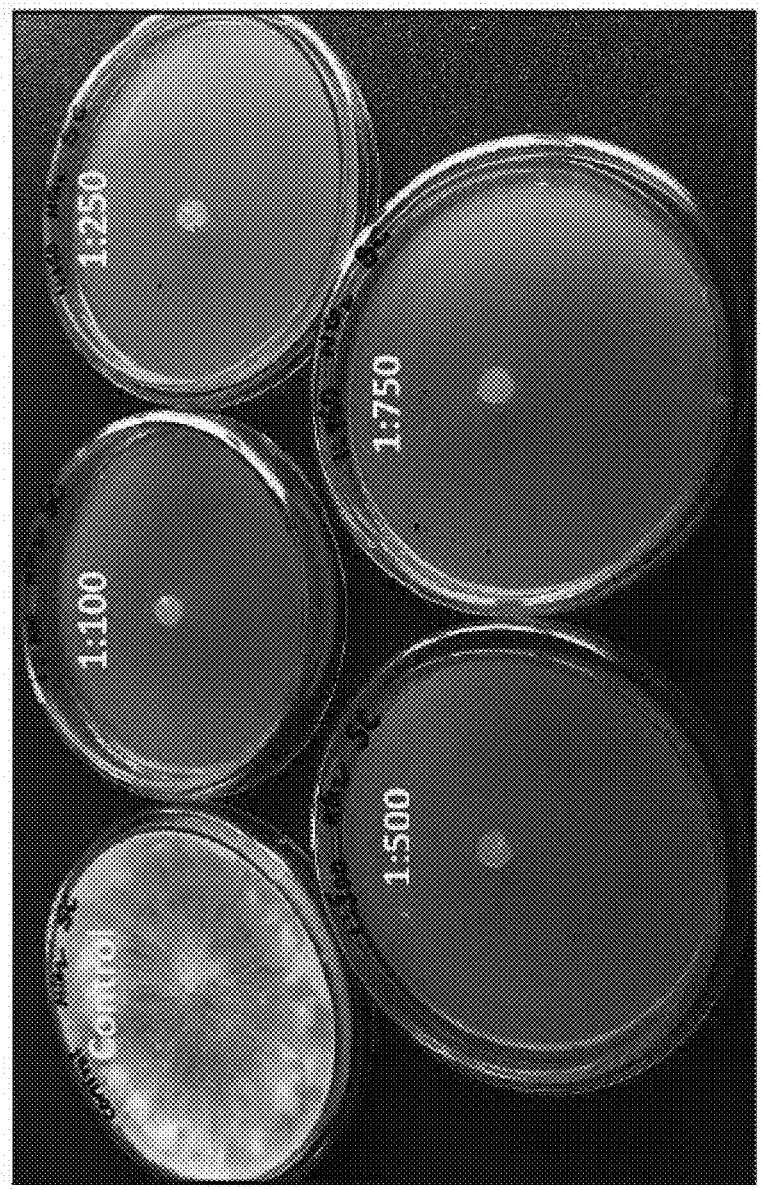
FIG. 15 is an illustration of an effect of NG 2 on *Sclerotium rolfsii*, in accordance with some embodiments.

FIG. 15 is an illustration of an effect of NG 2 on *Sclerotium rolfsii*, in accordance with some embodiments.

Figure 16:
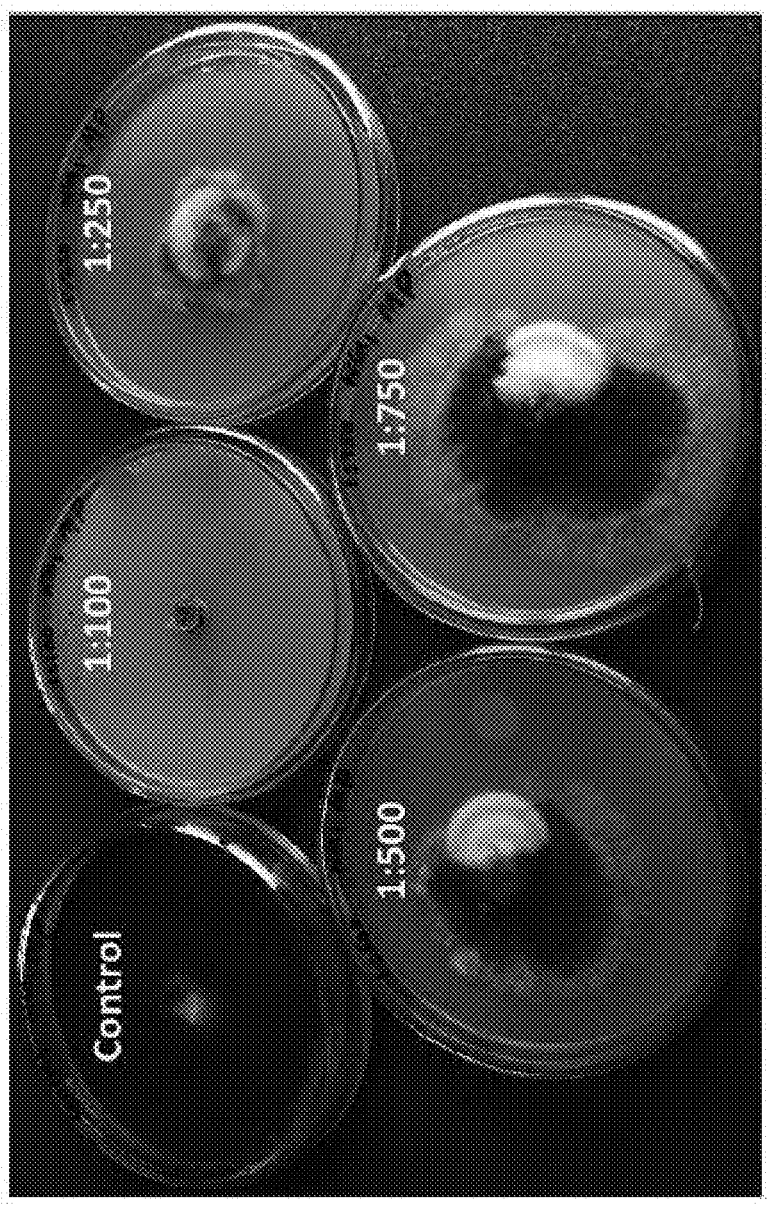
FIG. 16 is an illustration of an effect of NG 1 on *Macrophomina phaseolina*, in accordance with some embodiments.

FIG. 16 is an illustration of an effect of NG 1 on *Macrophomina phaseolina*, in accordance with some embodiments.

Figure 17:
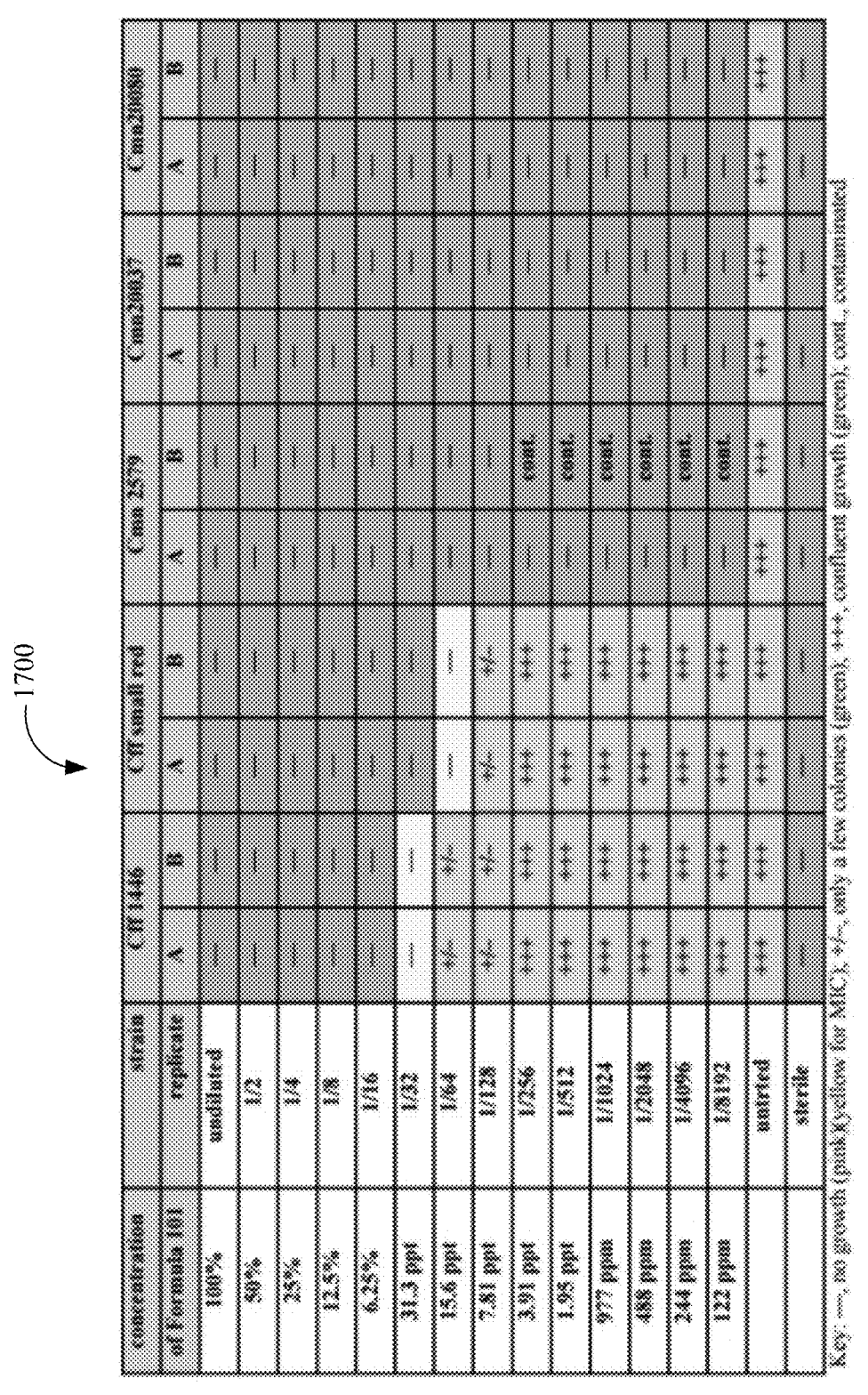

FIG. 17 is a table 1700 of an initial screen of pathogens vs. dilution of Formula S-101, in accordance with some embodiments. Further, the initial screen may include results at 96 hours after treatment for 22 hours. Further, the Formula S-101 may include the carbanions. Further, the initial screen may be associated with an evaluation of Formula S-101 and S-102 for activity against gram-positive plant pathogenic bacteria using pico-technology 340 pm/600 pm.

Further, Pico-technology 340 pm/600 pm Evaluation of Formula S-100 was effective in vitro at multiple concentrations in killing multiple isolates of agriculturally important Gram-positive plant pathogens. The bacteria tested in these assays were *Clavibacter michiganensis* subsp. *nebraskensis* (causal agent of Goss's wilt and blight of maize), Cl. mich. subsp. *michiganensis* (causal agent of bacterial canker of tomato), Cl. mich. subsp. *insidiosus* (causal agent of bacterial wilt of alfalfa), and *Curtobacterium flaccumfaciens* pv. *flaccumfaciens* (causal agent of bacterial wilt of dry bean). The three subspecies of *Clavibacter michiganensis* tested had indistinguishable sensitivities to Formula S-100 after 22 hours treatment ($2^{-14}=\frac{1}{16384}$, or 61 ppm), while *Curtobacterium flaccumfaciens* pv. *flaccumfaciens* was much less sensitive ($2^{-8}=\frac{1}{256}$, or 3.9 ppt). One replicate of a subset of strains was tested after 2 hours of treatment; this shorter exposure time was nearly as effective as 22 hours. Further, Formula S-100 was tested in vitro at multiple concentrations to assess its potential efficacy as a protection agent against important Gram-positive plant pathogenic bacteria in a greenhouse and field-grown crops. Further, materials and methods associated with the evaluation may include test organisms. Further, the test organisms may include *Clavibacter michiganensis* subsp. *nebraskensis* (Cmn) Disease: Goss' wilt and blight of maize. Further, the test organisms may include *Clavibacter michiganensis* subsp. *michiganensis* (Cmm) Disease: bacterial canker of tomato. Further, the test organisms may include *Clavibacter michiganensis* subsp. *insidiosus* (Cmi) Disease: bacterial wilt of alfalfa. Further, the test organisms may include *Curtobacterium flaccumfaciens* pv. *flaccumfaciens* (Cff) Disease: bacterial wilt of dry bean.

Further, Bacterial cultures had been maintained as lyophilized cultures or in Microbank vials (PRO-LAB Diagnostics, Canada) at −70° C. Culture suspensions, made from colonies grown on Tryptic Soy Agar, were grown for two to three hours in 10 ml Tryptic Soy Broth (Difco, Sparks, MD) at 27° C., sessile. The optical density of each culture was determined spectrophotometrically at 640.

Further, tested in this assay was the Formula S-100 non-toxic surfactant an amber and a viscous solution. Further, a modified Minimal Inhibitory Concentration (MIC) microbiological assay was used to determine levels of resistance of plant pathogens to this agent. Briefly, this method involves serial dilutions (1:2) of the test agent in TSB, a liquid growth medium. After the dilutions were made, an aliquot of bacterial suspensions was added to each tube, except for an uninoculated control. The tubes were incubated for 22 hours, shaking, at 27° C. Three 10 µL aliquots from each dilution were placed on the surface of a TSA plate, and the plates were incubated at 27° C. for 96 hours.

For the first assay, as shown in FIG. 17, the test agent was diluted in ten replicates: One milliliter of Formula S-100 concentrate was added to 1 ml of the first tube of the series and mixed; 1 ml of this tube was transferred to the second tube of 1 ml and mixed. The dilution process was repeated in subsequent tubes resulting in a final series which included the undiluted agent, 1:2, 1:4, 1:8, 1:16, 1:32, 1:64, 1:128, 1:256, 1:512, and 1:1024 dilutions.

Figure 18:
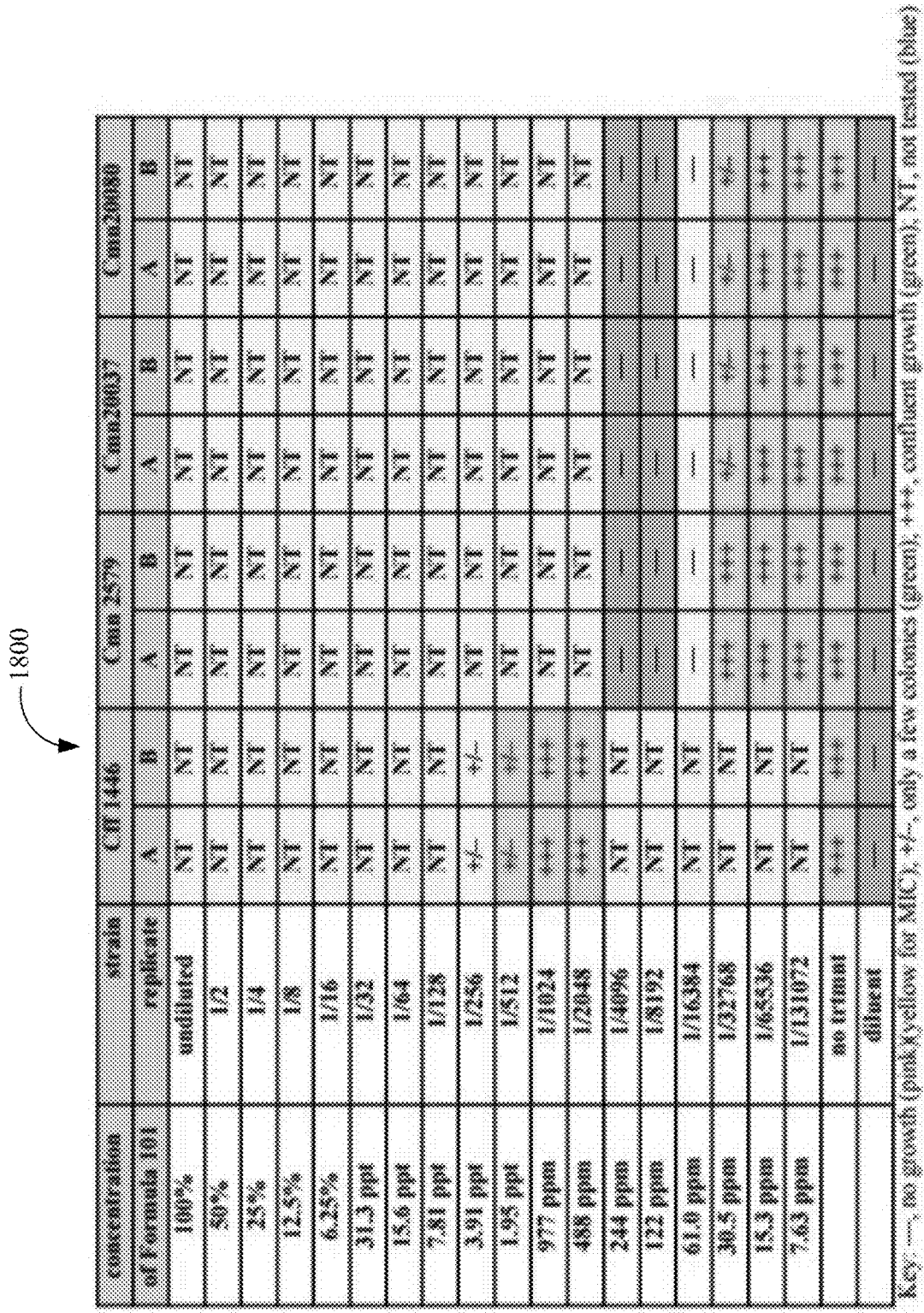
FIG. 18 is a table of a second screen of pathogens vs. dilution of Formula S-101, in accordance with some embodiments.
Figure 19:
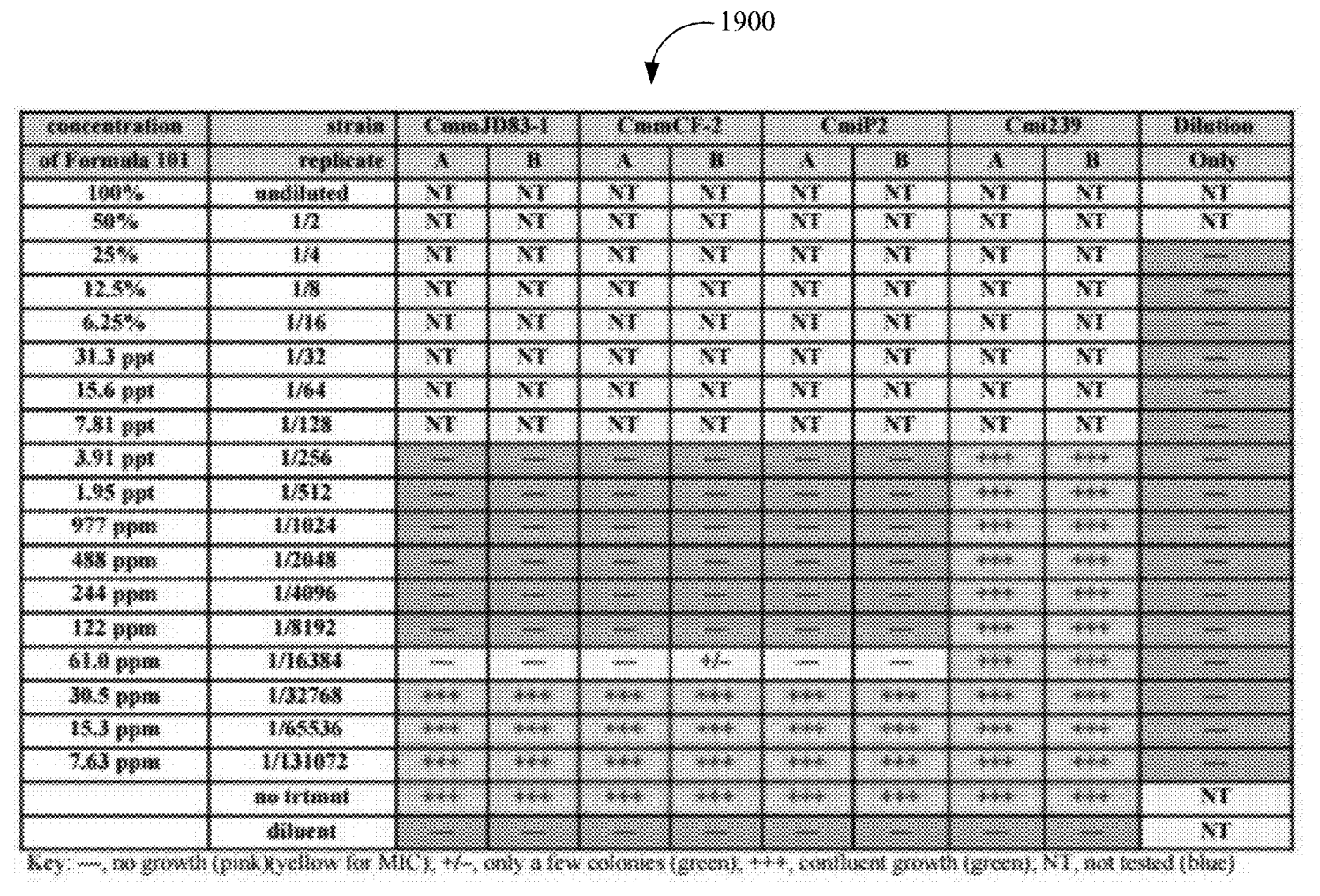
Figure 20:
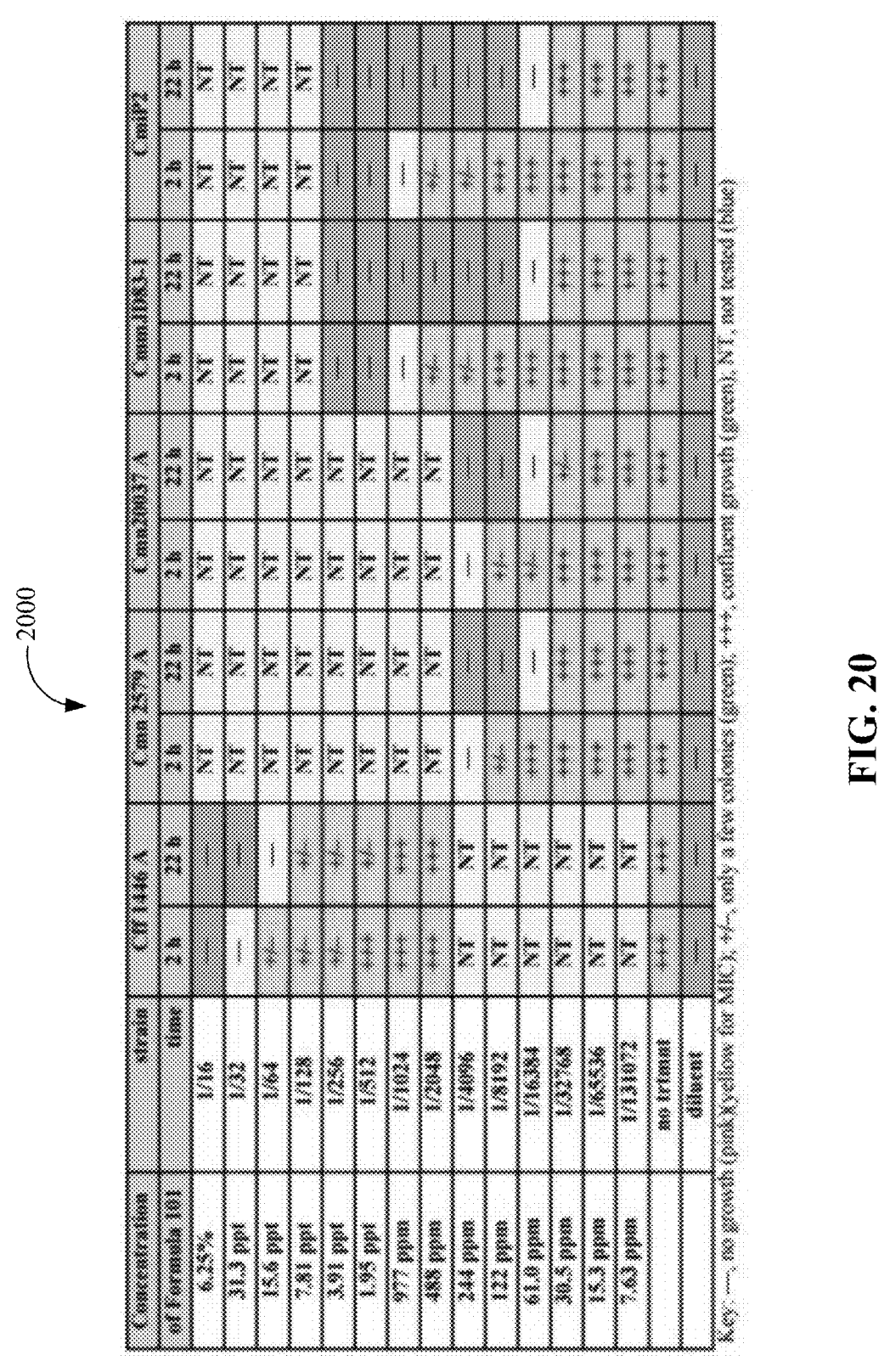
Figure 23:
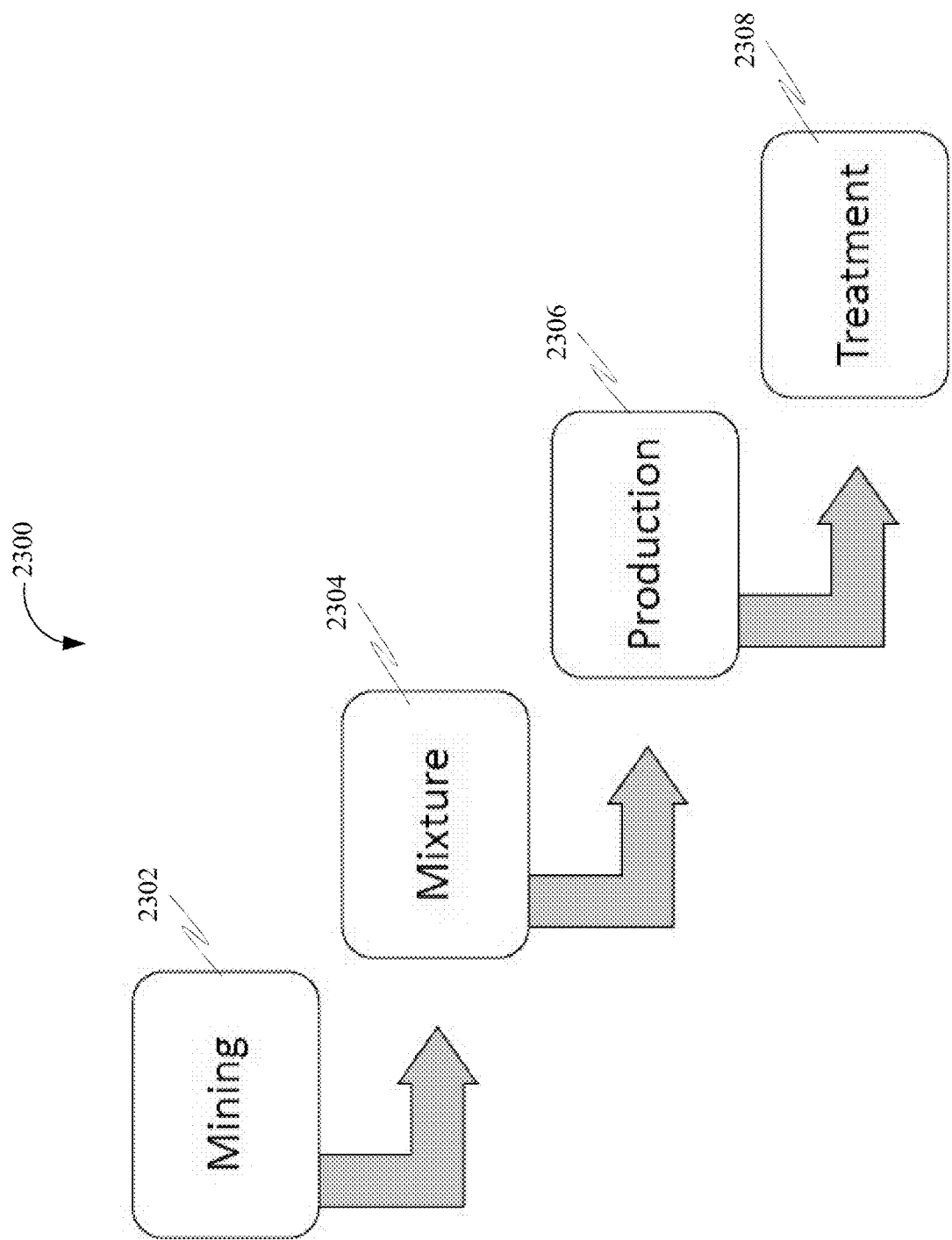
FIG. 23 is a flow diagram of a method of facilitating producing the medicine composition for treating diseases using the medicine composition, in accordance with some embodiments.
Figure 24:
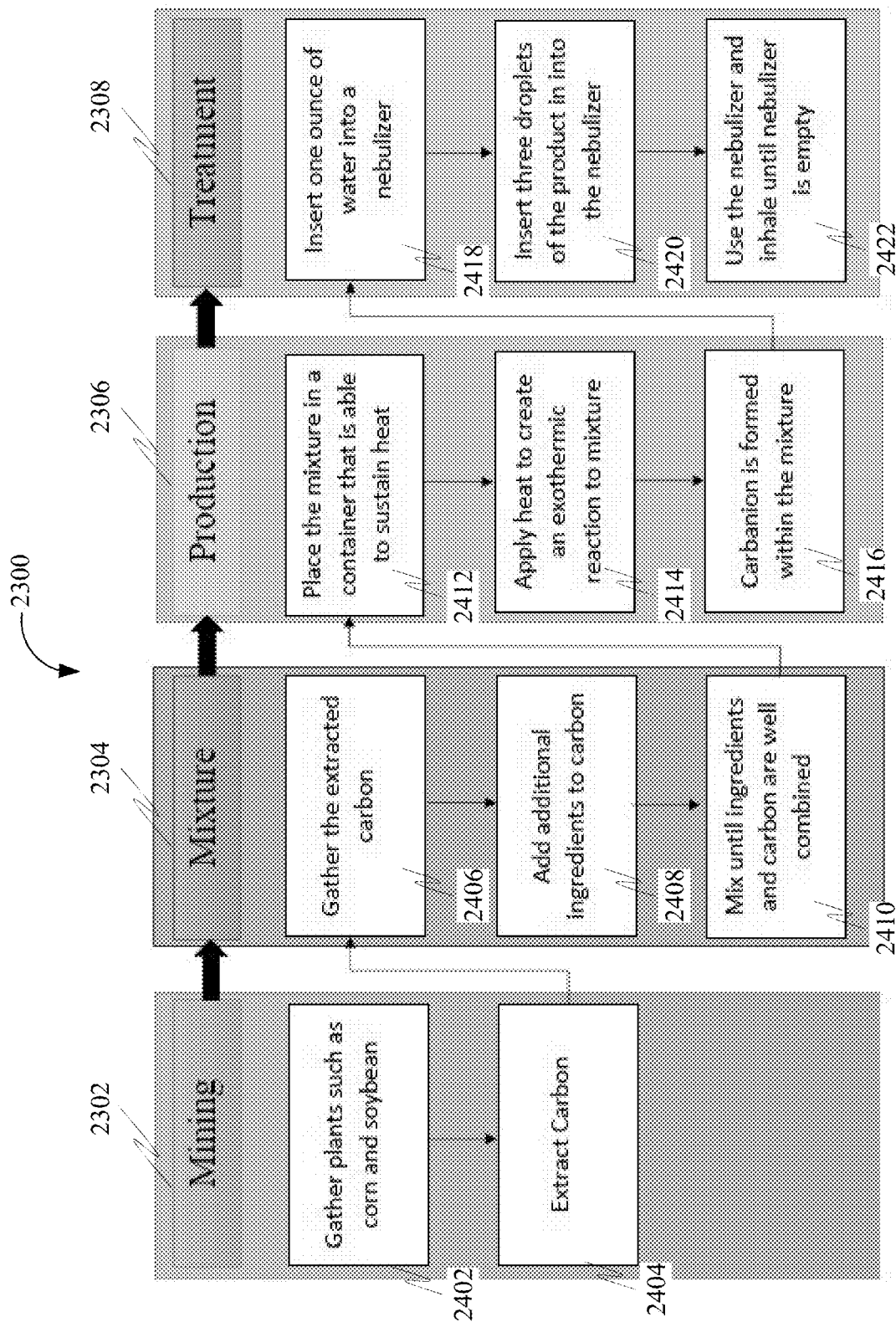
FIG. 24 is a flow diagram of the method of facilitating producing the medicine composition for treating the diseases using the medicine composition, in accordance with some embodiments.
Figure 25:
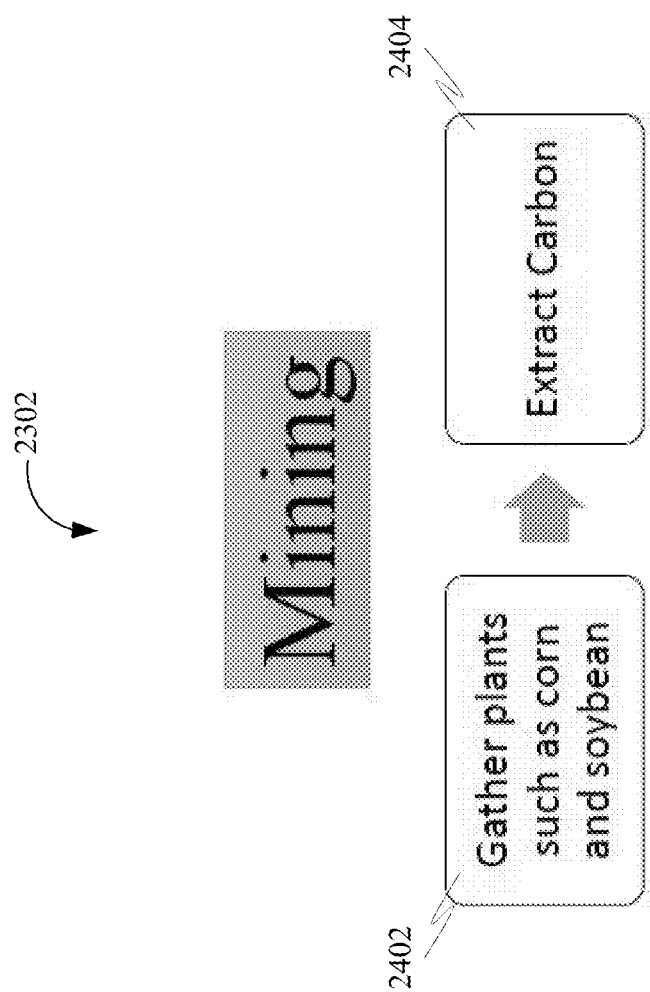
FIG. 25 is a flow diagram of the mining stage of the method, in accordance with some embodiments.
Figure 26:
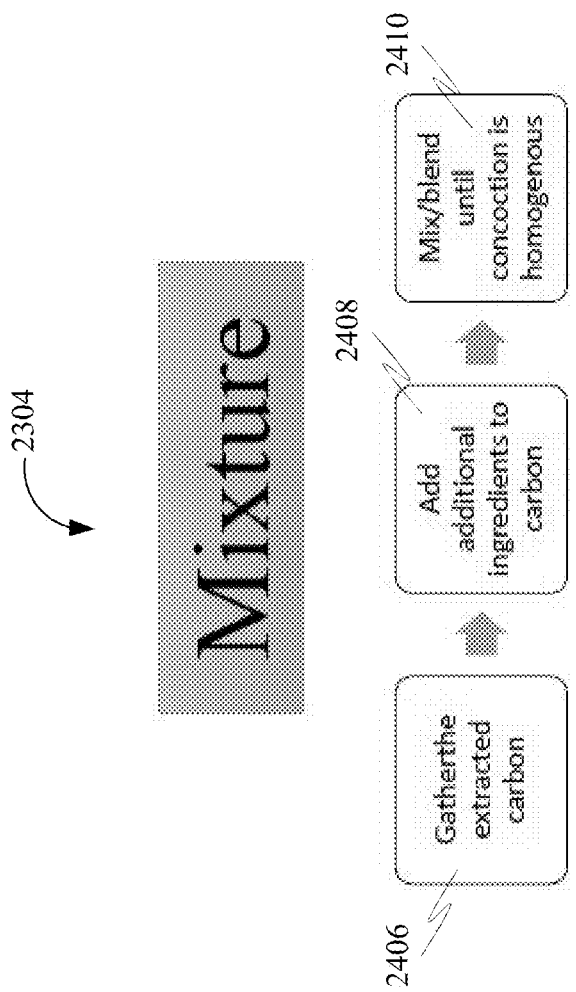
FIG. 26 is a flow diagram of the mixture stage of the method, in accordance with some embodiments.
Figure 27:
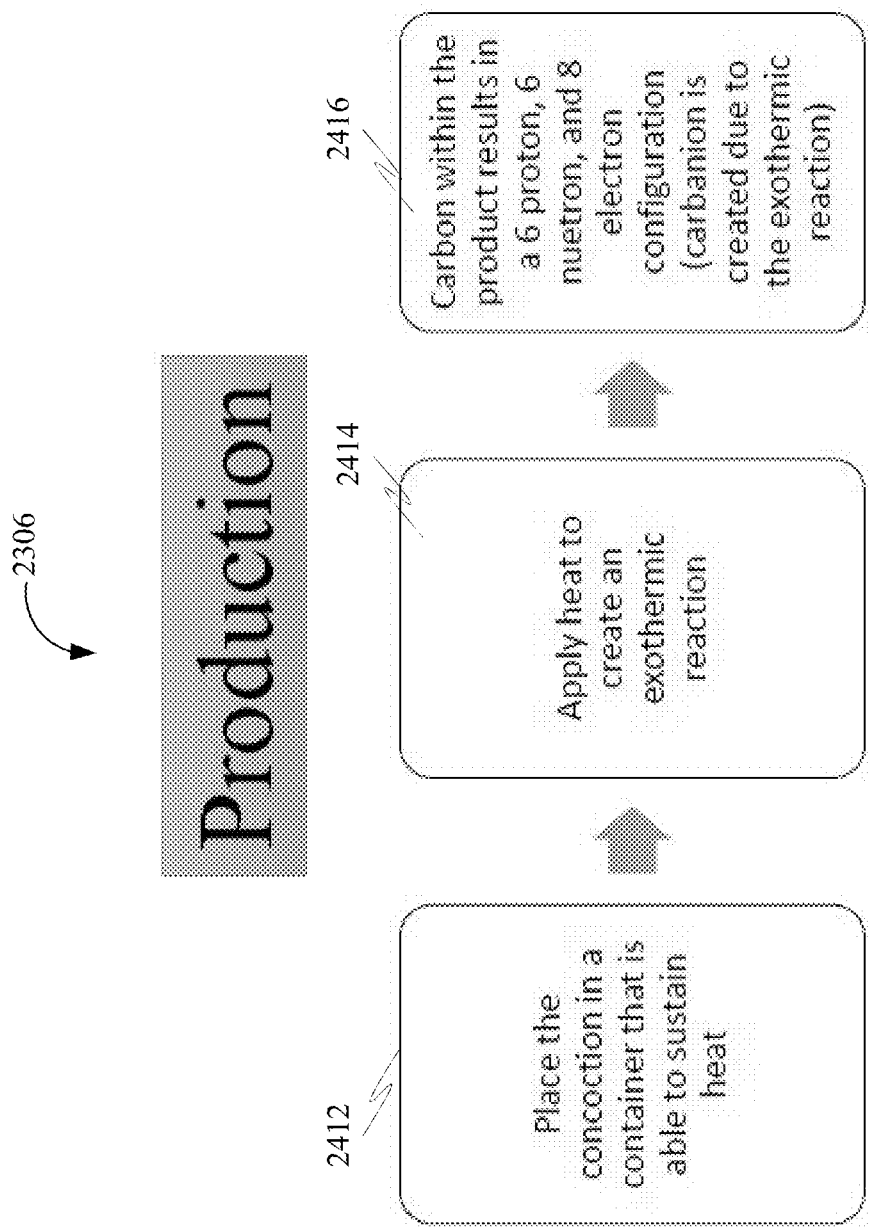
FIG. 27 is a flow diagram of the production stage of the method, in accordance with some embodiments.
Figure 28:
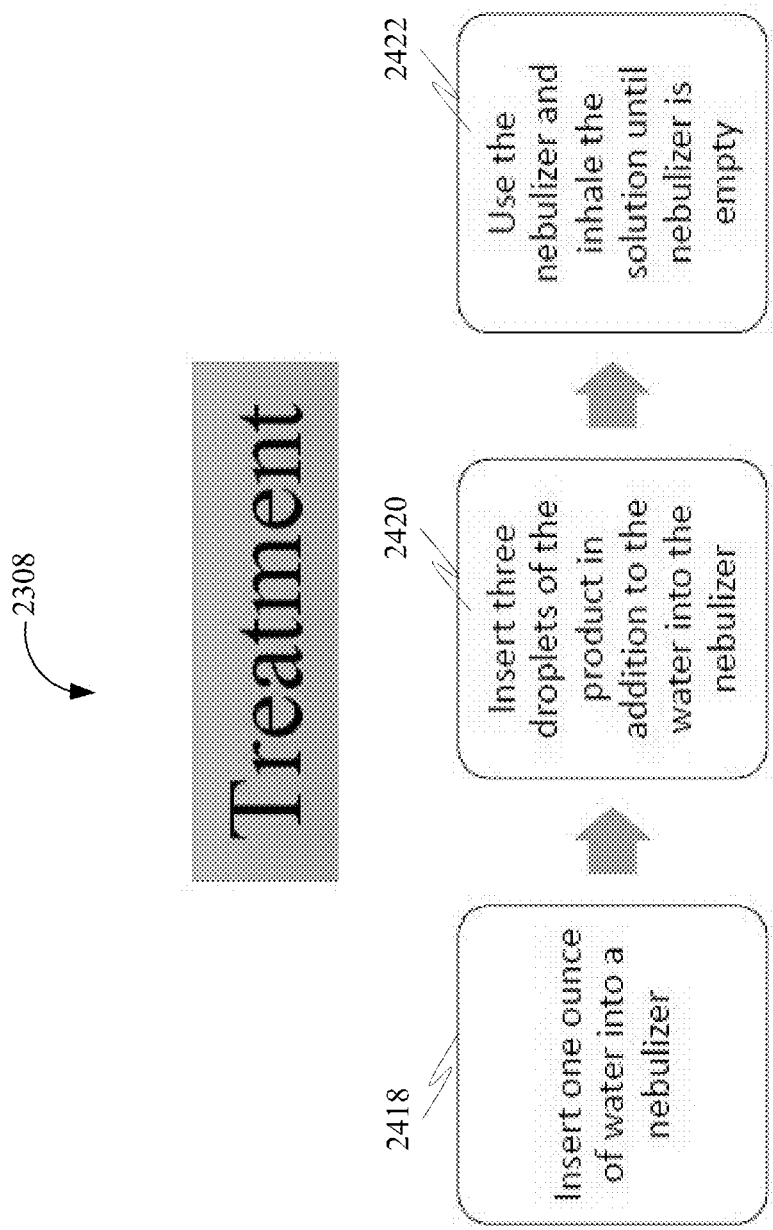
FIG. 28 is a flow diagram of the treatment stage of the method, in accordance with some embodiments.
Figure 30:
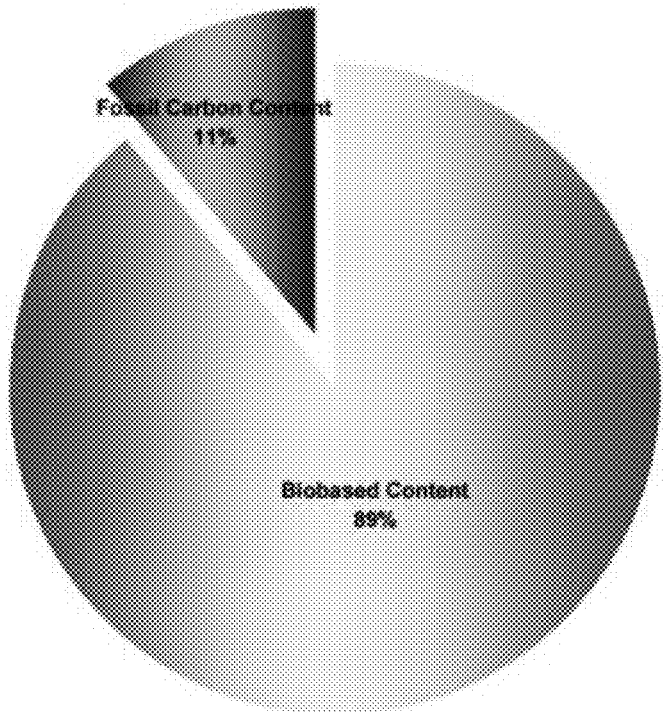
FIG. 30 is a chart of the lab results of the medicine composition, in accordance with some embodiments.
Figure 31:
FIG. 31 is a table of compositional elements of the medicine composition, in accordance with some embodiments.

For the second assay, as shown in FIG. 18, FIG. 19, and FIG. 20, the test agent was serially diluted as a single replicate, but in sufficient volume to dispense one-milliliter aliquots for each of the two replicates of each strain tested. This dilution series extended from the undiluted agent out to 1:131,072, in two-fold dilutions.

For each of the assays, control tubes were included: broth only and bacteria+broth (no agent). Additional control was included for the second assay: the dilution series with no bacteria added was checked for the absence of contaminating bacteria. Each bacterial isolate was tested in two replicate dilutions of the treatment.

The Minimum Inhibitory Concentration of an agent is the highest dilution or lowest concentration which prevents the growth of a bacterial culture. In a standard MIC assay, bacterial growth is assessed after incubation by comparing each tube of the dilution series visually or turbidimetrically against the control tube which contains the bacterial suspension with no test agent. We modified the MIC protocol by plating triplicate 10 f.iL aliquots of each test dilution and controls on TSA II™ Trypticase Soy Agar (BBL, Cockeysville, Md.) medium to validate and quantitate bacterial survival. The assay plates were incubated at 27° C., examined every 24 hours, and bacterial growth was recorded for controls and each dilution 96 hours after inoculation. The assay plates were kept for an additional 10-12 days at 27° C. to determine whether there were any "escapes" or additional surviving cells.

Further, the results of independent assays are presented in table format and attached. The growth of bacteria was recorded as positive (+) or negative (−) based on visible growth in the areas of inoculum (triplicate spots) on the agar plates. The minimum inhibitory concentration of agents is indicated on the tables by a yellow shading of cells; growth of bacteria by green shading.

The three subspecies of *Clavibacter michiganensis* tested had indistinguishable sensitivities to Formula S-100, not surprising given the extensively confirmed relatedness. *Curtobacterium flaccumfaciens* pv. *flaccumfaciens* was much less sensitive, a surprising result because this pathogen is closely related to the other three.

There are limited bacterial control agents currently registered for crop protection. Screening for cost-effective bactericides including bio-based, synthetic, and inorganic compounds frequently begins in the laboratory within vitro assays to evaluate the activity of the agent against target organisms in a non-plant system under standardized conditions. In vitro activity of an agent against a target organism, suggests potential but does not predict efficacy in plant disease control.

The assays of Formula S-100 demonstrated its in vitro activity at 22 hours against multiple isolates of four important bacterial pathogens of important crops. Even at very low concentrations, Formula S-100 was highly active against Cmn, the causal agent of Goss's wilt and blight of maize, Cmm, the causal agent of bacterial canker of tomato and Cmi, the causal agent of bacterial wilt of alfalfa, as shown in FIG. 18 and FIG. 19. Except for one of the two strains of Cmi (which may be an atypical strain), these pathogens did not survive at a concentration of 61 ppm (MIC=1:16384), which is impressive. Previously, Cmn was tested against S-102, and in those tests, the pathogen did not survive a concentration of 980 ppm (or 0.098%) (MIC=1:1024).

Formula S-100 demonstrated a reduced activity at 22 hours against Cff, the agent of bacterial wilt of bean (MIC=1:64 for one isolate and MIC=1:128 for the other). These results for Cff were similar to the results for S-102 vs. Cff.

The activity of Formula S-101 at two hours was tested for one of the two replicates for two strains of Cmn, one strain of Cmm, one strain of Cmi, and the Cff strain, as shown in FIG. 20. The results at two hours, limited as the result was by assaying only one replicate of fewer strains, were similar to the results at 22 hours, but the additional incubation time did appear to allow lower concentrations of Formula S-100 to be more effective relative to the two-hour incubation.

Based on these promising results, areas for further study might include a testing activity of Formula S-101 or S-102 (or both) at several concentrations in a greenhouse and field-grown plants to evaluate efficacy and phytotoxicity in planta (in plants), selection of a delivery method of agent and pathogen, and time sequence studies to assess death rate of bacterial pathogens when the agent is applied prior to or after plant inoculation.

FIG. 18 is a table 1800 of a second screen of pathogens vs. dilution of Formula S-101, in accordance with some embodiments. Further, the second screen may include results at 96 hours after treatment for 22 hours.

FIG. 19 is a table 1900 of the second screen of pathogens vs. dilution of Formula S-101, in accordance with some embodiments. Further, the second screen may include results at 96 hours after treatment for 22 hours.

FIG. 20 is a table 2000 of a subset of the second screen of pathogens vs. dilutions of Formula S-101, in accordance with some embodiments. Further, the second screen of the subset may include results at 96 hours after treatment for either 2 or 22 hours.

FIG. 21 is a table 2100 of therapeutic options for fungal lung infections.

FIG. 22 is a table 2200 of antifungal treatment options.

FIG. 23 is a flow diagram of a method 2300 of facilitating producing the medicine composition for treating diseases using the medicine composition, in accordance with some embodiments. Further, the medicine composition may include the carbanions. Further, the method 2300 may include four stages 2302-2308. Further, the four stages 2302-2308 may include a mining stage 2302, a mixture stage 2304, a production stage 2306, and a treatment stage 2308.

FIG. 24 is a flow diagram of the method 2300 of facilitating producing the medicine composition for treating the diseases using the medicine composition, in accordance with some embodiments. Further, at 2402, the mining stage 2302 may include gathering plants. Further, at 2404, the mining stage 2302 may include extracting carbon. Further, at 2406, the mixture stage 2304 may include gathering the extracted carbon. Further, at 2408, the mixture stage 2304 may include adding additional ingredients to the carbon. Further, at 2410, the mixture stage 2304 may include mixing until the ingredients and carbon are well combined. Further, at 2412, the production stage 2306 may include placing the mixture in a container that may be able to sustain heat. Further, at 2414, the production stage 2306 may include applying the heat to create an exothermic reaction to the mixture. Further, at 2416, the production stage 2306 may include forming of the carbanions within the mixture. Further, at 2418, the treatment stage 2308 may include inserting one ounce of water into a nebulizer. Further, at 2420, the treatment stage 2308 may include inserting three droplets of the product comprising the carbanion into the nebulizer. Further, at 2422, the treatment stage 2308 may include using the nebulizer and inhaling until the nebulizer is empty.

FIG. 25 is a flow diagram of the mining stage 2302 of the method 2300, in accordance with some embodiments.

FIG. 26 is a flow diagram of the mixture stage 2304 of the method 2300, in accordance with some embodiments.

FIG. 27 is a flow diagram of the production stage 2306 of the method 2300, in accordance with some embodiments.

FIG. 28 is a flow diagram of the treatment stage 2308 of the method 2300, in accordance with some embodiments.

FIG. 29 is a table 2900 of compositional elements of the medicine composition, in accordance with some embodiments.

FIG. 30 is a chart 3000 of the lab results of the medicine composition, in accordance with some embodiments.

FIG. 31 is a table 3100 of compositional elements of the medicine composition, in accordance with some embodiments.

Although the present disclosure has been explained in relation to its preferred embodiment, it is to be understood that many other possible modifications and variations can be made without departing from the spirit and scope of the disclosure.

What is claimed is:

1. A medicine composition for facilitating treating organs of a mammal, the medicine composition comprising:
    carbanions, wherein a carbanion of the carbanions comprises a carbon atom, wherein the carbon atom comprises a formal charge of −1; and
    a diluting agent, wherein the diluting agent is capable of combining with the carbanions for forming at least one appliable form of the medicine composition, wherein a ratio of the diluting agent to the carbanions by volume ranges from 512:1 to 32:1, wherein the combining facilitates applying of the at least one appliable form of the medicine composition to at least one organ of the mammal.

2. The medicine composition of claim 1, wherein the ratio of the diluting agent to the carbanions by the volume is 284:1.

3. The medicine composition of claim 1, wherein the ratio of the diluting agent to the carbanions by the volume is 189:1.

4. The medicine composition of claim 1, wherein the ratio of the diluting agent to the carbanions by the volume is 57:1.

5. The medicine composition of claim 1 further comprising an elemental composition in a ratio to the carbanions by volume, wherein the ratio of the elemental composition to the carbanions by the volume is 1:9.

6. The medicine composition of claim 5, wherein the elemental composition comprises oxygen, hydrogen, nitrogen, phosphorus, potassium, calcium, magnesium, sulfur, iron, silicon, aluminum, chlorine, and manganese.

7. The medicine composition of claim 1, wherein each carbanion of the carbanions is capable of creating an electromechanical reaction with an organic material of at least one organism present on the at least one organ of the mammal based on the applying of the at least one appliable form of the medicine composition, wherein the creating of the electromechanical reaction disassembles the organic material of the at least one organism for eliminating the at least one organism, wherein the eliminating of the at least one organism facilitates the treating of the at least one organ of the mammal.

8. The medicine composition of claim 1, wherein the carbanions are derived from at least one organic material, wherein the at least one organic material is associated with at least one part of at least one plant, wherein the at least one plant comprises a corn plant, wherein the at least one part of the corn plant comprises a leaf, a stem, a grain, a root, and a cob.

9. The medicine composition of claim 1, wherein the diluting agent comprises at least one cream, wherein the at least one cream comprises a shea butter.

10. The medicine composition of claim 1, wherein the diluting agent comprises at least one moisturizing element.

11. A method for facilitating treating organs of a mammal using a medicine composition, the method comprising:
    transforming, using at least one application device, the medicine composition into at least one appliable form, wherein the medicine composition comprises carbanions and a diluting agent, wherein a carbanion of the carbanions comprises a carbon atom, wherein the carbon atom comprises a formal charge of −1, wherein the diluting agent is capable of combining with the carbanions for forming the at least one appliable form of the medicine composition, wherein a ratio of the diluting agent to the carbanions by volume ranges from 512:1 to 32:1; and
    applying, using the at least one application device, at least one dosage of the at least one appliable form of the medicine composition on at least one organ of the mammal based on the transforming, wherein the applying of the at least one dosage of the at least one appliable form of the medicine composition facilitates the treating of the at least one organ of the mammal.

12. The method of claim 11, wherein the at least one application device comprises a nebulizer, wherein the at least one organ comprises at least one lung, wherein the at least one appliable form of the medicine composition comprises an aerosol, wherein the transforming comprises aerosolizing the medicine composition into the aerosol, wherein the applying comprises delivering the aerosol to the at least one lung of the mammal.

13. The method of claim 11, wherein the at least one application device comprises an emulsifier, wherein the at least one organ comprises skin, wherein the at least one appliable form of the medicine composition comprises an emulsion, wherein the transforming comprises emulsifying the medicine composition into the emulsion, wherein the applying comprises covering the skin of the mammal with the emulsion.

14. The method of claim 11 further comprising generating, using the at least one application device, the at least one dosage of the at least one appliable form of the medicine composition, wherein the applying of the at least one dosage of the at least one appliable form of the medicine composition is further based on the generating of the at least one dosage.

15. The method of claim 11, wherein the at least one dosage of the at least one appliable form of the medicine composition comprises one ounce of water and at least three drops of the carbanions, wherein the diluting agent comprises the water.

16. The method of claim 11, wherein the treating of the at least one organ comprises eliminating at least one organism from the at least one organ causing at least one disease in the at least one organ of the mammal based on the applying, wherein the eliminating comprises disassembling an organic material of the at least one organism based on an interaction of the carbanions with the organic material based on the applying.

17. The method of claim 11, wherein the treating of the at least one organ comprises regenerating at least one tissue of the at least one organ of the mammal based on the applying.

18. The method of claim 11, wherein the at least one dosage of the at least one appliable form of the medicine composition is associated with a dosing frequency, wherein the dosing frequency comprises three times a day for at least one three days, wherein the applying of the at least one dosage of the at least one appliable form of the medicine composition with the dosing frequency facilitates the treating of the at least one organ.

19. The method of claim 11, wherein the applying of the at least one appliable form of the medicine composition is associated with an applying duration, wherein the treating of the at least one organ is based on the applying of the at least one appliable form of the medicine composition for the applying duration.

20. The method of claim 11, wherein the at least one appliable form of the medicine composition comprises a solution, wherein the solution is appliable to the at least one organ using at least one application method, wherein the applying of the solution of the medicine composition to the at least one organ facilitates the treating of the at least one organ.

* * * * *